United States Patent [19]
Eisele et al.

[11] Patent Number: 5,175,431
[45] Date of Patent: Dec. 29, 1992

[54] HIGH PRESSURE SELECTED ION CHEMICAL IONIZATION INTERFACE FOR CONNECTING A SAMPLE SOURCE TO AN ANALYSIS DEVICE

[75] Inventors: Fred L. Eisele; Harald Berresheim, both of Norcross, Ga.

[73] Assignee: Georgia Tech Research Corporation, Atlanta, Ga.

[21] Appl. No.: 674,548

[22] Filed: Mar. 22, 1991

[51] Int. Cl.$^5$ ............................................... H01J 49/26
[52] U.S. Cl. ................................... 250/288; 250/282
[58] Field of Search ............... 250/288 R, 288 A, 287, 250/282, 283; 73/23.35

[56] References Cited

U.S. PATENT DOCUMENTS

| | | | |
|---|---|---|---|
| 3,589,171 | 6/1971 | Haley | 73/23.1 |
| 3,639,757 | 2/1972 | Caroll et al. | 250/282 |
| 3,935,452 | 1/1976 | Prince | 250/283 |
| 4,137,750 | 2/1979 | French et al. | 73/23 |
| 4,378,499 | 3/1983 | Spangler et al. | 250/287 |
| 4,517,461 | 5/1985 | Crandall | 250/282 |
| 5,012,052 | 4/1991 | Hayes | 250/288 |

Primary Examiner—Jack I. Berman
Assistant Examiner—James Beyer
Attorney, Agent, or Firm—Hurt, Richardson, Garner, Todd & Cadenhead

[57] ABSTRACT

A high pressure interface device for connecting a gas chromatograph to a mass spectrometer having a high pressure laminar flow, flow tube ion reactor cell containing an isolated ionization source and an axial sample injection port in which specific ion species formed by radioactive bombardment of gas mixture are reacted with gaseous samples to result in an ionized gaseous sample. When coupled to a multistage pumped mass spectrometer, this invention makes possible detection sensitivities of trace sample species in the subparts per trillion range and under proper condition does not need calibration.

28 Claims, 10 Drawing Sheets

HIGH PRESSURE SELECTED ION CHEMICAL IONIZATION INTERFACE FOR CONNECTING A SAMPLE SOURCE TO AN ANALYSIS DEVICE

BACKGROUND OF THE INVENTION

1. Field of the Invention

The invention relates generally to an interface for use in connecting a gas chromatograph or other gas introduction means to a mass spectrometer or other mass measurement means in order to allow for greater detection sensitivities in the mass measurement means. The invention relates specifically to a laminar flow, flow tube ion reactor cell in which specific ion species formed by radioactive bombardment of a gas mixture are reacted with a gaseous sample introduced into the tube, forming ionized species of the gaseous sample, which are then introduced into a collisional dissociation chamber, if needed, and then into a multistage pumped spectrometer, resulting in a substantial increase in the detection sensitivity for the mass spectrometer.

2. Prior Art

The coupling of a gas chromatograph to a mass spectrometer is known in the prior art. However, the sensitivity of the output of the mass spectrometer is limited both by the method of ionization and by the quality of input from the gas chromatograph (GC). The choice of GC operating conditions, sample separating column and sample separating stationary phase can greatly enhance or detract from the output to the mass spectrometer. The sensitivity of the coupled gas chromatograph/mass spectrometer system is limited by, among other things, the nonspecific ionization of sample species, background noise arising from effluent from the chromatograph column, the number and concentration of sample species contained in the sample gas, the loss of sample on the column material, the efficiency of the GC in separating interfering sample species, and the finite peak width of each sample species eluting from the gas chromatograph.

There have been attempts at developing methods or apparatuses for connecting a chromatograph to a mass spectrometer in such a manner so as to separate undesired chemicals from desired chemicals in the chromatograph prior to introducing the sample to the mass spectrometer. Reducing the complexity of the sample matrix introduced to the mass spectrometer reduces the complexity of the mass spectra created by the mass spectrometer. One such method and apparatus is described in the patent to Caroll et al, U.S. Pat. No. 3,639,757, which discloses an apparatus and method for the analysis of discrete samples. Caroll et al discloses the injection into and volatization of a sample within a first chamber. The sample is ionized with reacting ions produced in the first chamber and the reacted sample ions are directed by a drift field to a second chamber having a lower pressure than the first chamber. Within the second chamber, the ions are analyzed.

The disadvantages of the Caroll patent include a relatively short reaction time and relatively low pressure chambers resulting in lower sensitivity within the mass analysis device. Also due to the relatively short reaction time, the efficient use of the sample is relatively low and the selection by proton or electron affinity is diminished. Additionally, old sample gas remains in the first chamber, thus resulting in a memory effect within the first chamber. Further, uniform laminar flow is not achieved due to the presence of electrodes and guard rings within the first chamber. The ion chemistry in the Caroll device which finally leads to the product ion of interest also can be very complex, making the apparatus difficult to calibrate. The Caroll device also lacks a dissociation chamber to remove clusters which will cause unwanted peaks in the mass spectra.

A second apparatus and method for increasing the sensitivity for detecting low concentrations of sample gases is described in Ketkar, S. N. et al., Atmospheric Pressure Ionization Tandem Mass Spectrometric System For Real-Time Detection Of Low-Level Pollutants In Air, 61 Analytical Chemistry 260-264 (1989). The Ketkar article describes an ionization system for detecting very low levels of contamination in air. The specific system described uses a point-to-plane corona discharge with means to produce primary ions which ionize the trace molecules in a sample gas. A low pressure declustering region helps remove water cluster ions and a tandem mass spectrometric system is used to detect trace molecules.

There are several disadvantages inherent in the Ketkar system, including several of the disadvantages listed above. Relatively short reaction times and relatively low pressures decrease the sensitivity of the mass analysis device. The relatively high temperature ion reaction region may cause fragmentation or radical formation of unwanted species within the reaction region. Further, the Ketkar apparatus does not act as a wall-less reaction region, thus resulting in the possibility of a memory effect. Again, ion chemistry is complex and variable, and thus the instrument is difficult to calibrate. The low pressure cluster removal means has comparatively low efficiency for removing these clusters.

The patent to the University of Toronto, U.K. Patent No. 1582869, discloses a gas curtain device and method for transferring matter between a gas and a vacuum. A second patent to the University of Toronto, U.K. Patent No. 1584459, based on the above patent, discloses a method of focussing and dissociating trace ions. The first patent includes a flow tube having a centrally located axial electrode to induce ion drift into a gas curtain to facilitate the transfer of the sample ions and not buffer gas into a mass analyzer. The present invention has been used in conjunction with devices similar to this one; however the central electrode, on which sample gas species could be absorbed and later desorbed, was found to be unnecessary, and for relatively clean sample gas the curtain gas also is not needed. When the present invention was used in conjunction with a dissociation device, a separate chamber for dissociating clustered ions was found advantageous.

Each of these components has a distinct disadvantage when compared to the present invention. First, the centrally located electrode may disrupt the axial flow of the sample gas and prevent uniform laminar flow through the reaction region. Second, in contrast to the relatively high pressure laminar flow in the present invention, a drift field is required. In the present invention interface, sample gas ions will naturally remain near the axis constrained by diffusion in the relatively high pressure flow tube until they reach the relatively low pressure collision chamber or analyzer. Third, the prior art requires a gas curtain. In contrast, the clean buffer gas and preseparated sample gas in the present invention, uninterrupted by the presence of any axial electrode or other surfaces, obviates the need for a gas curtain, as the clean, dry buffer/sample gas presents no problems upon entering the collision chamber or analyzer region. Fourth, the prior art are of use downstream from where the selected ion chemical-ionization process takes place; that is, downstream from where the present invention is located. This prior art is useful primarily with the present invention as shown in FIGS. 3 and 4 herein.

Atmospheric pressure ionization mass spectrometry (APIMS) has proved to be an extremely sensitive method for detecting gas phase species at ultratrace levels. Currently, most of these methods are employed only for analysis of bulk phase samples. Therefore, their extreme sensitivity is rather limited to only those species having relatively high proton or electron affinities. The typical hierarchy of potentially stable product ion species present in gas samples limits the present applicability of chemical ionization mass spectrometry methods to relatively few, very stable species. Sensitive detection of species having relatively low proton or electron affinities can be achieved by coupling atmospheric pressure chemical ionization/MS with a technique such as gas chromatography (GC) which separates the component(s) of interest in the sample matrix from interfering high affinity species. Thus, a potentially large number of species may be detected with extreme sensitivity using combined GC/APCI/MS. However, to this date, the powerful capabilities of this technique have hardly been recognized.

The range of species measured by chemical ionization techniques also has been limited by the relatively crude manner in which these techniques have been previously applied. Most chemical ionization techniques directly ionize the sample gas being studied using either radioactive alpha or beta sources or a corona discharge. This poses several problems and drawbacks:

1. Both alpha and beta irradiation of a sample gas impart only half of the energy into the production of ions. The ionization efficiency is even lower for corona discharge.

2. Both alpha and beta sources produce metastable and neutral radical species at a rate at least as high and probably higher than the initial ion production rate. Unless the ions are extracted by strong electric fields, most ions are lost by ion-ion recombination, potentially forming additional radical species.

3. Even if ions are extracted from the ion source region, the initially formed neutral radicals are not. They are only removed by the gas flow through the ion source region and have a significant time to react with the trace species in the sample gas. Radical production rate for a 10 mc $^{63}$Ni beta source of 0.1 - mc $^{241}$Am source can reach $10^9$–$10^{10}$/sec which at gas flows of 10 cm/sec through the source region can result in a concentration of $10^8$–$10^9$ radicals or chemically altered species. In most applications this causes major interferences preventing a sensitive detection of the sample species in the low parts-per-trillion (pptrv) or sub-pptrv range.

4. Corona sources can cause at least as much alteration of the sample chemistry as direct radioactive sample irradiation.

Compared to the prior art, the present invention allows for the separation of the ionization and reaction regions. The present invention allows for the preparation of a single selectable initial reactant ion species reducing or in many cases removing the need for constant calibration. The present allows for longer reaction times and higher pressure chambers thus resulting in higher sensitivity for the mass analysis means, a more efficient use of sample, and the creation of an essentially wall-less laminar flow reaction region, greatly reducing or eliminating the reactions on the tube walls and possible memory effects. A low temperature ion reaction region results in essentially no fragmentation or radical formation within the reaction region. Laminar flow is achieved in the present invention through the use of turbulence-reducing screens and the elimination of guard rings or electrodes. The specific collisional dissociation chamber developed for the present invention results in a higher removal rate for weakly bound clusters such as water clusters while minimizing the dissociation of core ion species.

The present apparatus does not suffer from the difficulties encountered with previous chemical ionization techniques because it does not directly ionize the gas being sampled. Instead, the present apparatus forms ion species in a buffer gas and allows sufficient time for most metastable or radical species to be removed before they are allowed to interact with the gas sample being analyzed. The present technique also differs from conventional chemical ionization methodology in that it uses a single specific core ion species to react with the trace compound to be measured. This is accomplished by forming the initial reactant ions in a tailor made buffer gas. Thus, the terminal ion to be detected is formed in a single known reaction (often a fast proton or electron exchange reaction) with the compound to be detected. Therefore, the detection sensitivity of the measurement is known or can be measured, and is dependent on one reaction rate constant and the reaction time. It is not dependent on the other unknown constituents of the gas being sampled. Thus, the system need not be calibrated each time new sample gas is added. If the species to be detected forms a sufficiently stable ion such that once formed it will not react further, then the present device often can be operated in conjunction with a mass spectrometer on a continuous basis (no GC). This is possible as long as the initial reactant can be maintained as the predominant ion species present by: (1) choosing a sufficiently stable reactant ion; (2) reduction of reaction time; (3) sample dilution; or (4) some combination of the above possibilities.

The present invention makes possible the direct detection and quantification of gaseous samples in air at parts-per-trillion (pptrv) and sub-pptrv levels involving no preconcentration. Generally, previous methods used to analyze gaseous samples using gas chromatography/mass spectrometry (GC/MS) involve detection systems with much lower sensitivities (typical commercial MS detectors: typically in the ppb range and above) than the present invention and, therefore, require preconcentration of the gaseous sample for levels in the lower pptv range. Preconcentration (for instance adsorption on solid adsorbent, or cryogenic trapping) bears several serious disadvantages such as, for example, the potential occurrence of artifact reactions of the sample gas with other reactive species during preconcentration or injection of the preconcentrated sample and taking time. In contrast, the present invention is essentially free of interferences, is highly sensitive and highly selective, and involves direct identification of the species of interest by single or tandem mass spectrometry.

SUMMARY OF THE INVENTION

The invention is an interface between a gaseous sample introduction means such as a gas chromatograph and a mass detection and measurement means, such as a mass spectrometer. The invention comprises a novel high pressure flow tube device into which a gaseous sample is introduced which reacts with a previously introduced specific ion species. A reactant ion species is created by ionizing specific trace gas parent neutral species (trace gas) carried into the flow tube by a cleaned buffer gas, which is generally a chemically inert carrier gas such as nitrogen ($N_2$) containing the trace gas, such as about one part per billion water vapor ($H_2O$), or about 100 parts per million oxygen ($O_2$). The buffer gas is introduced to the flow tube, established into a laminar flow, and ionized by a low intensity radioactive source. The gaseous sample, generally from a gas chromatograph, is injected axially preferably along the central axis of the flow tube. Within the flow tube, the gaseous sample encounters and reacts with the reactant ion species which can be specifically selected for use with the chosen gaseous sample. The high sensitivity of the present apparatus is achieved by allowing each specifically prepared ion to undergo many billions of collisions with the sample gas in the laminar flow reactor region. Upon reaching the distal end of the flow tube, the ionized gaseous sample passes into a collisional dissociation chamber where most of any weakly bound water clusters attached to the ionized sample are collisionally dissociated. The now relatively simple ion spectrum containing primarily the initial reactant ion (such as $H_3O^+$) and a lesser amount of the species under study will be measured using a mass spectrometer.

The carrier gas is purified by passing through a cryogenic trap, typically a high pressure (about 20 psi) liquid nitrogen trap. In some cases the trace gas also is passed through this trap. Otherwise, the trace gas is then added to the carrier gas to produce the buffer gas. Optionally, the trace gas, for example $O_2$, can be photolyzed in a quartz photolysis cell to form $O_3$ subsequent to the cryogenic trap. The carrier gas is then introduced into the proximal end of the flow tube (the flow tube entrance). Within the proximal end of the flow tube is a back flange with uniformly spaced inlet holes through which the buffer gas first flows, causing the buffer gas to uniformly fill the flow tube. The buffer gas then passes through at least one and generally two or more turbulence-reducing screens to establish a uniform and laminar flow pattern within the reaction area of the flow tube. After passing through the turbulence-reducing screens, the buffer gas encounters a radioactive source, generally an alpha or beta emitter, which bombards the buffer gas, ionizing the buffer gas which results in the ionization of the trace gas, largely by proton and electron exchange. The back flange and turbulence-reducing screens (the laminar buffer gas flow region), and the radioactive source (ion source region) are located within the flow tube prior to the end port of the sample injection tube, allowing the buffer gas to become uniformly dispersed and ionizied prior to encountering the sample gas.

The sample gas, generally the eluent from a gas chromatograph but often simply a bulk sample of ambient air, is injected into the flow tube downstream from the laminar buffer gas flow region and ion source region. The sample encounters and reacts with the carrier gas, now containing a single ion species (the ionized trace gas), forming relatively stable sample species ions and trace gas atoms or molecules. Due to the radially uniform nature of the buffer gas flow and the axial injection of the gaseous sample at a similar velocity to the buffer gas flow leads to little turbulence, the sample species ions tend to travel axially in the center of the flow tube, and because of the high pressure radial diffusion from the axis is relatively slow. The concentration of sample species ions formed is relatively small ($\leq 10\%$) compared to the concentration of initial reactant ions. Since the reaction times, the reaction rate constant for reactant ion/sample species of interest, and the concentration ratio of reactant ion/sample ion are either known or measurable, the sensitivity of the above apparatus can be both known and fixed at predetermined values for any specific compound as long as the initial reactant ion remains the primary species present in the ion spectrum. This has been accomplished for $NO^-_3$ in the OH measurement described below in Example IV, and has been closely approached in Examples I and II. The flow tube reactor cell operates at pressures on the order of one atmosphere or higher to increase sensitivity.

At the distal end of the flow tube is the flow tube exit aperture leading to the collisional dissociation chamber. The sample species ions travel through the flow tube exit aperture into the collisional dissociation chamber, if used, while the bulk of the carrier gas leaves the flow tube through exhaust gas ports. Also due to the axial nature of the flow of the sample species ions, the input into the collisional dissociation chamber comprises a relatively high concentration of sample gas. Optionally, as the sample species ions reach the end of the flow tube, they may be refocused toward the central axis of the flow tube and accelerated toward the exit aperture by a converging electrostatic field. This field is produced by maintaining a potential difference between the flow tube walls and the exit aperture. This field forces the sample species ions close to the flow tube axis and into a neutral carrier gas (not shown) just in front of the exit port.

The collisional dissociation chamber (which is largely needed only if $H_2O$ and other polar molecules are not removed from the sample gas) is designed specifically to collisionally dissociate water clusters weakly bound to the sample species ions. The chamber, which typically operates at about 0.1 torr, consists of a vacuum-tight enclosure containing several electrically insulated guard rings maintained at potentials to produce an approximately uniform electrical field along the axis of the chamber. The sample species ions, shed of the weakly bound water clusters, then are introduced to a mass spectrometer for measurement. Although the removal of water clusters is not crucial to the operation of the invention, it is beneficial to allow detection of gaseous sample ions at only a single mass and not a series of masses consisting of multiple additives of the sample ion species and water molecules. Thus, the resulting ion spectrum created by the mass spectrometer is simple, containing only one ion mass per core ion species, and the number of ions of the same sample species is accumulated in one large peak in the mass spectrometer because the ions are not divided up among multiple additive mass peaks.

OBJECTS OF THE INVENTION

Accordingly, it is an object of the present invention to provide:
    a means for removing or reducing the need for calibrating a GC/MS system;
    a means for increasing the detection sensitivity of a mass spectrometer;

a means for interfacing a gas injection means such as a gas chromatograph to a mass measurement means such as a mass spectrometer;

a means for interfacing a gas chromatograph to a mass spectrometer utilizing a flow tube chemical ionization reactor allowing the uniform and laminar flow of the reacting species along the axial length of the flow tube;

a means for ionizing a sample gas species in a relatively high pressure environment in the absence of metastable and radical formation virtually eliminating interferences by unwanted radical and metastable species;

a chemical ionization process which involves a single reactant ion and product ion such that the measured reactant ion/product ion concentration ratio depends only on a fixed reaction rate, a known reaction time, and sample concentration thus removing the need for calibration;

a means in which a reactant ion may be chosen which has a proton or electron affinity relatively close to, but still below, that of the species to be measured, thus minimizing interfering reactions;

an essentially wall-less flow tube reactor by using laminar flow conditions in a relatively large diameter, high pressure flow tube reactor resulting in a reduction of memory effects and minimal dilution of the sample gas;

a means for introducing a sample species ion into a mass spectrometer by sampling only a small percentage of the total number of ions from the central portion of a symmetric ion swarm thus greatly reducing or eliminating wall reactions;

a means for introducing sample species ions to a mass spectrometer in a purely gas phase;

a means for detecting the quantity of sample species ions at only a single mass and not at a series of masses which would include integer multiples above the core ion mass resulting from the presence of interfering gases, that is the number of ions observed at each peak will be larger because the ions are not divided up among several different mass peaks; and a means for measuring and identifying species at concentrations below one part per trillion, provided the species have sufficient proton and/or electron affinities.

These objects, and other objects, features and advantages of the present invention, will become apparent to one skilled in the art when the following Detailed Description of a Preferred Embodiment is read in conjunction with the accompanying Figures, in which like reference numerals represent corresponding parts throughout the several drawings.

DETAILED DESCRIPTION OF A PREFERRED EMBODIMENT

1. Apparatus

Figure 1:
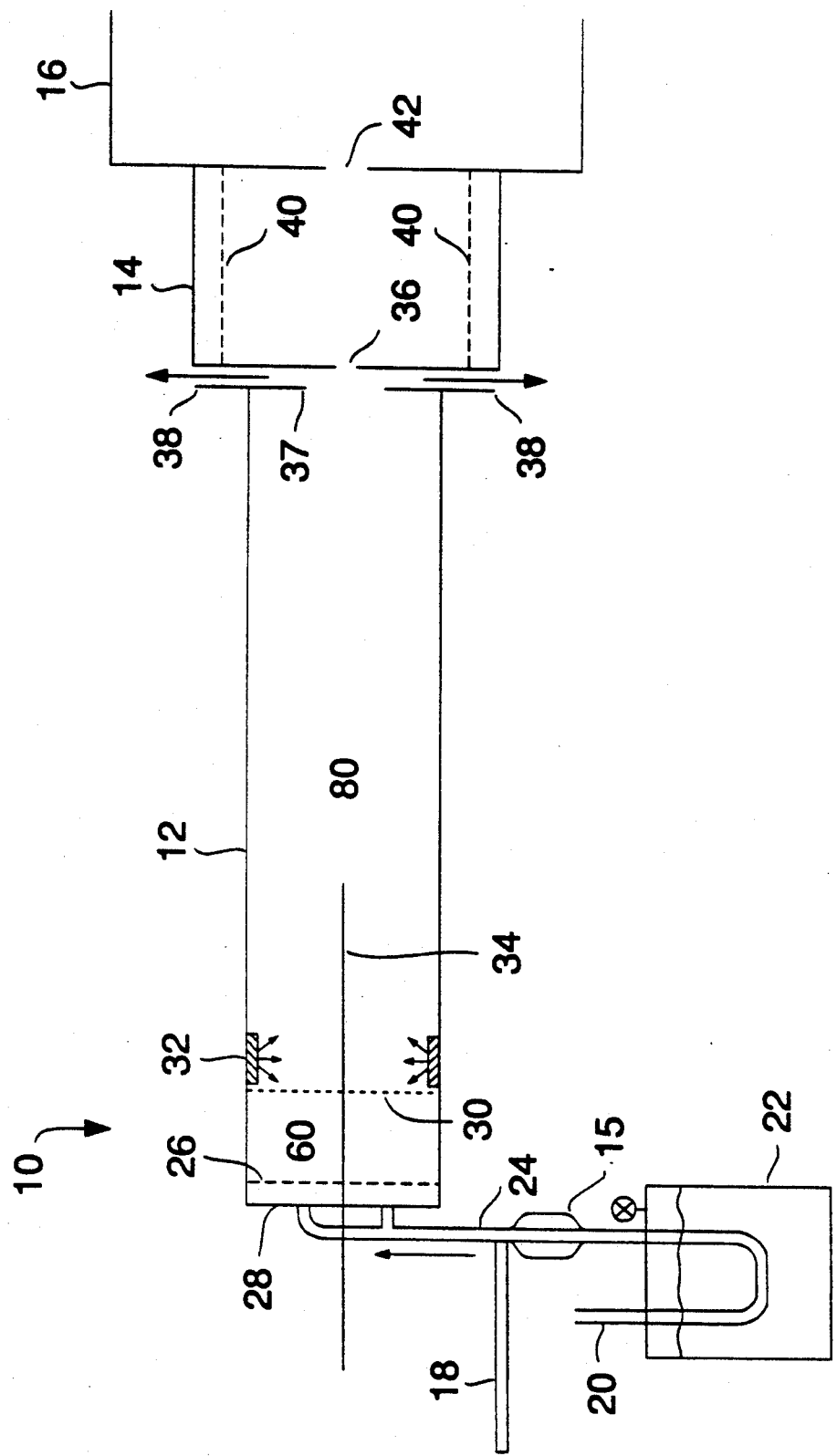
FIG. 1 is a schematic of the apparatus of the present invention.

Referring now to FIG. 1, the interface 10 of the present invention comprises a high pressure flow tube 12, in which specific ion species are formed by either alpha or beta bombardment of a tailor-made buffer gas mixture comprising a trace gas and a carrier gas. These ions then react with a gaseous sample introduced through injector 34 and into the flow tube 12. The flow tube 12 optionally is attached to a low pressure collision dissociation chamber 14. When coupled to a multistage pumped mass spectrometer 16, this interface 10 makes possible detection sensitivities in the sub-parts-per-trillion (sub-pptrv) range for a large number of chemical compounds. When used in relation to describing the flow tube 12, the term high-pressure is defined as pressures on the order of magnitude of 1 atmosphere or higher, as the flow tube 12 is capable of suitable operation at such pressures.

FIG. 1 shows the major components of the invention. In general, the cylindrical flow tube 12 is electrically conducting and has a smooth bore to minimize gas turbulence. It also is of sufficient diameter that diffusion of the ion species between the wall and center of the tube 12 (or the converse) is not significant in the time required for the sample gas to travel the length of the tube 12. Although the diameter of the flow tube 12 is not critical, the diameter is to a certain extent dependent on the residence time necessary for sufficient reaction of the sample gas with the ion species contained in the buffer gas. Generally, longer residence times necessitate a larger diameter. The flow tube 12 used in the following Examples was about one inch (1") in diameter.

A cryogenic trap 22 is used to purify the carrier gas. Nitrogen is the preferred carrier gas because it is abundant and inexpensive. Other carrier gases, such as the noble gases, also are suitable. The cryogenic trap 22 is generally a high pressure liquid nitrogen trap (about 20 psi) which can be baked out for 24–48 hours or longer to reduce the presence of polar and high electron and proton affinity species in the carrier gas down to the low ppt range. The cryogenic trap 22 may be pressurized to a pressure greater than that of the flow tube 12 to prevent trapping out the nitrogen buffer gas.

The trace gas is added to the cleansed carrier gas via a trace gas input 18 to form the buffer gas, unless the trace gas already is in the carrier gas. The buffer gas mixture comprising a carrier gas, typically $N_2$, containing the trace gas, such as, for example, a few parts-per-billion (ppb) $H_2O$ (for positive operation) or approximately 100-1000 parts-per-million (ppb) $O_2$ (for negative ion formation), enters the laminar buffer gas flow region 60 of the flow tube 12 from the buffer gas input 24 through a back flange 26, at the proximal end 28 of the flow tube 12, having a series of uniformly spaced holes to more uniformly distribute the buffer gas within the flow tube 12. The buffer gas next passes through fine metal turbulence-reducing screens 30 or other suitable means to establish a uniform and laminar flow pattern. The exact mesh size of the turbulence-reducing screens 30 is not critical as long as a mesh with a relatively regular pattern is used. A finer mesh will help reduce turbulence. The mesh size of the turbulence reducing screens 30 used in the following Examples was about 100 lines per inch. Other methods which form a laminar gas flow within a short distance are suitable, such as the use of a plurality of holes in the back flange 26, the use of mesh substitutes, or the use of a region 60 long enough to allow the establishment of a laminar flow prior to both ionization and contact with the sample gas.

Immediately after the last screen 30, the buffer gas enters the ion source region 70 where it is ionized by a radioactive source such as an alpha or beta emitter coated on a cylinder or ring 32 concentric with the inside the flow tube 12. For example, if a radioactive coating of Nickel-63 on the order of 10 micro-curies is used, an ion concentration of about $2-4 \times 10^5$ ions/cm$^3$ in the central region of the flow tube 12 is produced. Various known radioactive sources which are sufficient to create the desired level of ionization are acceptable. It is preferable to have a very low intensity radioactive source which produces a stable emission, and is just strong enough to ionize the buffer gas with minimal formation of metastable or radical species. In this regard, corona sources are less desirable. X-ray sources also are suitable. The buffer gas should remain in the ion formation region 70 for a time sufficient for the majority of any metastable or radical species to be eliminated before the sample gas enters the specific ion/molecule reaction region 80. It is important that the ionization of the buffer gas occurs in an isolated region 70 of the flow tube 12 where no sample gas is present, preferably just prior to encountering the sample gas. Depending on the desired flow tube 12 residence time, an ion concentration of about $10^5-10^7$ ions/cm$^3$ is formed. Generally, residence times range from about 0.01 seconds to 3.0 seconds or more, although shorter and longer residence times are suitable.

The introduction of a sample into the flow tube 12 is accomplished by an axial injection needle 34, which can be resistance heated for low vapor pressure species if desired. The needle 34 would generally operate from about room temperature (about 22° C.-32° C.) to about 400° C., with 200° C. being the preferred maximum such that a Teflon-type coating or tubing may be used on the inside surface of needle 34 without melting to allow injection of samples through the needle 34 which are incompatible with the needle 34 material. The injection mass flow rate through the needle 34 orifice is typically only a few percent (0.1-5%) of the total mass flow rate in the tube 12. The sample species is mixed rapidly with the buffer gas/ion species mixture within a few (<10) millimeters from the tip of needle 34 along the flow tube 12 axis by both local turbulence near the needle 34 orifice and by diffusion. The ionized buffer gas travels coaxially in the flow tube 12 at a gas flow velocity approximately equal to that of the injected sample gas, allowing the ions in the buffer gas to mix with the sample gas largely by molecular diffusion. The sample gas dilution is relatively small and the maximum concentration of the sample gas remains on the flow tube axis. The sample species react with the ions present, typically within about one second, while diffusion from the center of the flow tube 12 is relatively slow. In this time the ions will typically undergo about $10^9-10^{10}$ collisions with the sample species.

The positive or negative ions initially formed are quickly converted into $H^+\cdot(H_2O)_n$ or $O_2^-\cdot(H_2O)_m$, respectively (where n or m depends on the $H_2O$ content of the gas used, and on temperature and pressure). These secondary ion species are formed generally in less than 0.1 second in the corresponding gas mixtures, and are thus the predominant ion species present, as the gas/ion mixture flows past the end of the sample injection needle. Unless a sample is injected into the flow tube 12, these secondary ions remain as the primary ion species present when the gas/ion mixture reaches the exit aperture 36 of the flow tube 12. The residence time of the gas/ion mixture in the flow tube 12 can be regulated and is typically on the order of 0.1 to several (3 or more) seconds, depending on the sensitivity desired. On their way to the tube exit aperture 36, some of the ions are gradually destroyed by ion-ion recombination. However, even after several seconds, ion concentrations are still on the order of $10^5$ ion/cm$^3$.

The sample gas may have water molecules in it if not removed in the GC. As the sample gas expands through the injection needle 34, the gas cools adiabatically and reacts with the water, causing clusters of water to become weakly bound to the sample gas. These water clusters for the most part are removed from the sample gas in the collisional dissociation chamber 14 as discussed below. The presence of water in the sample species ions introduced to the mass spectrometer 16 will cause peaks in the mass spectra occurring at multiples of 18 (the molecular weight of water) which are unwanted.

A complex sample matrix such as ambient air contains many gaseous components and it may be desirable to measure the quantity of only one of the gaseous components. The trace gas to be included in the buffer gas can be or is sometimes selected by choosing a specific gas which, when ionized by the radioactive source 32, will react with the desired gaseous component, and not most others of the gaseous components contained in the ambient air sample. As a result of the separation of the buffer gas introduction 24 and the sample gas injection 34, a single specific ground state ion species can be produced in an inert buffer gas. The identity of the reactant ion species produced in the ion source is controlled by the trace gas added to or contained in the buffer gas. By using the known or measurable reaction rate between the trace gas and the gaseous component, the quantity of gaseous component in the ambient air, GC effluent, or other sample can be determined from the ratio of reactant ion/product ion concentration, reaction rate constant, and reaction time. In this manner, only two ion species are involved in the measurement, including the gaseous component of interest. A major depletion of the reactant ion signals that the technique is no longer linear, and typically signals that other unwanted species in the sample gas are at too high a concentration and that flow conditions or sample gas purity needs to be adjusted. As long as the initial reactant ion concentration is not dramatically depleted by other species no major measurement error is introduced by the presence of these unknown and unwanted ion species.

With an ion concentration of about $10^5$ ions/cm$^3$, a one second reaction time (about $10^9$-$10^{10}$ ion-molecule collisions), and a mass identified detection sensitivity of about 1 ion/cm$^3$ (for atmospheric pressure and an integration time of 60 seconds) the described device (in combination with a mass spectrometer system) offers extremely high detection sensitivity (up to 1 part in $10^{14}$) for compounds forming stable ions in the flow tube 12. Typically, the criteria to be met for a species to be readily observable in the positive ion spectrum is that its proton affinity is at least several kcal/mole above that of the parent ion (the proton affinity of $H_2O$ is about 166 kcal/mole). Species to be detected in the negative ion spectrum must have a higher electron affinity than that of the parent ion (the electron affinity of $O_2$ is about 10 kcal/mole) or in some cases a greater acidity than the ion parent. Detection in the positive ion spectrum typically is based on a proton exchange of the sample gas with $H^+.(H_2O)$ Detection in the negative spectrum typically is based on proton or electron transfer reactions but can also proceed through more general two-and three-body ion-molecule reactions which lead to more stable terminal ion species.

The relatively stable sample ions formed during the reaction between the trace gas ions and the sample gas are transported down the length of the flow tube 12 in the same manner as the trace gas ion species, except that the removal rate by ion-ion recombination and diffusion is somewhat different from that of the trace gas ions. Typically, the injected sample only alters a small fraction of the ions present in either the positive or negative spectrum and has essentially no effect on the other (opposite polarity) spectrum. Thus, the number of trace gas ions reacting with the injected compound(s) to form specific new ion species are proportional to the concentration of reactive sample species injected into the flow tube 12. If the ion species produced from the injected compounds becomes a significant portion of the total number of ions and there is more than one type of sample ion present, then the ion residence time in the flow tube 12 must be reduced or the sample gas be better separated or further diluted. The corresponding reduction in lifetime can be accomplished by increasing the carrier gas flow through the flow tube 12.

The flow tube 12 becomes effectively wall-less by using laminar flow conditions in a relatively large diameter, high pressure flow tube, and by sampling only a very small percentage of the total number of ions from the central portion of a symmetric ion swarm. Since wall effects are thus eliminated (no wall losses, catalytic wall reactions, or species desorption from the wall), the ion and neutral chemistry occurring in the flow tube 12 can be characterized as being purely gas phase. Further, this chemistry is essentially free of any memory effect from compounds previously injected into the flow tube 12.

The resulting wall-less laminar flow through the flow tube 12 allows the sample species injected along the flow tube 12 axis (in the center of the flow of ionized buffer gas) to react along the axis of the flow tube 12 without diffusing to the flow tube 12 walls. The relatively low residence time of the species in the flow tube 12 also helps prevent the species from contacting the flow tube 12 walls. The laminar flow and relatively low residence time results in the ability of the invention to input into the mass spectrometer 16 species that under turbulent conditions would partially stick to the reaction chamber (flow tube 12) walls. Further, the sample species flows in an axially symmetric pattern and the sample ions are relatively easily removed through the exit aperture 36 into the collisional dissociation chamber 14.

The use of a very dry (less than about 1 ppb $H_2O$), clean buffer gas is desired as such a buffer gas can, if used in conjunction with a dry GC effluent gas, eliminate the need for a collisional dissociation chamber 14. Optimum results are obtained when extremely clean carrier gases and trace gases are used to create the buffer gas. The cryogenic trap 22 helps achieve this. Sample separation devices such as gas chromatograph columns having a clean output are desirable. Prior to use, the gas chromatograph column should be heat conditioned and cleaned of all extraneous matter and, if possible, heated while being purged with the clean buffer gas. The gas chromatograph column stationary phase should have as low bleed (low volatility) as possible. Preferably a monomolecular coated phase should be used. Effective GC separation of the sample species also may be achieved by gas-solid chromatography (GSC) using porous polymer materials with very low column bleed.

If a less dry, less clean sample gas is used, the ions in the buffer/sample gas mixture should be separated out into a dry buffer gas prior to introducing the sample ions into the collisional dissociation chamber 14 by, for example, a curtain gas and a converging electrostatic field. See Eisele, F. L., 54 Int'l J. Mass Spec. and Ion Processes. 119-126 (1983)(curtain gas); Eisele, F. L., 91 J. Geophys. Res. 7897-7906 (1986)(collision chamber), both of which are incorporated herein by this reference and made a part hereof. Generally, the curtain gas and converging electrostatic field are needed only if the buffer gas, carrier gas, trace gas, or sample species contains a great deal of $H_2O$, other polar molecules or highly corrosive gases.

Virtually all of the ions reaching the exit aperture 36 of the flow tube 12 become hydrated to some extent if water is not removed initially from the sample gas. In practice, with a flow tube 12 operating at or above one atmosphere of pressure, maintaining the $H_2O$ concentration at a sufficiently low level (around 1 ppb) to prevent significant ion hydration is relatively difficult. In addition, as ions pass through the exit aperture 36 and expand along with the gas in which they are contained, the subsequent adiabatic temperature decrease induces further ion hydration (or ion clustering) if $H_2O$ concentrations are greater than about 0.1%. The chamber 14 into which these hydrated ions enter after passing through the aperture 36 is specifically designed to collisionally dissociate weakly bound $H_2O$ clusters. The first application of the present collisional dissociation chamber 14 has been described previously. See F. L. Eisele, Identification of Tropospheric Ions, 91 J. Geophys. Res. 7897-7906 (1986), incorporated herein by this reference and made a part hereof. The use of such a molecular cluster dissociating device is of most use when the present invention is operated in a crude form, for example, with no preseparation of sample gas such as by GC, with multicomponent sample gases, uncleaned buffer gases, and wetter buffer gases.

This preferred chamber 14, shown in FIG. 1, is a low pressure drift tube which typically is operated at about 0.1 torr and offers a proportionally larger number of collisions between ions at a given E/N value (electric field intensity divided by gas number density). It has been found that operating the chamber 14 at higher than about 0.01 torr and lower than 1.0 torr, with a preferred range of between about 0.05 and 0.2 torr, produces optimum results. Pressures higher than about 1.0 torr result in a loss of signal and pressures below about 0.01 torr result in fewer collisions unless the chamber is undesirably long. The central core of the ion cloud produced near the flow tube 12 axis passes through the exit aperture 36 (typically about 20-200 micrometer diameter depending on the pumping capability of the mass spectrometer), into the attached collisional dissociation chamber 14.

The only gas which enters the chamber 14 comes from the flow tube 12 by passing through the flow tube exit aperture 36 (along with the ions contained in it). Within the chamber 14, water clusters weakly bound to the sample species ions are removed, allowing relatively pure sample species ions to be introduced to the mass spectrometer 16. The purer the sample species ions introduced, the greater the detection sensitivity of the mass spectrometer 16, and the cleaner the mass spectra produced. The bulk of the buffer gas is exhausted by a radially outward motion through the much larger exit duct 38 (while ions pass through aperture 36 and are focused through the aperture 42) at the distal end of the flow tube 12. Removal of the bulk of the buffer gas is to minimize turbulence in the flow tube 12 and so as not to disturb the central axial flow. More detailed descriptions of the pumping system and both single and tandem mass spectrometers which can be used in conjunction with this collisional dissociation chamber 14 are given in 93 J. Geophys. Res. 7897 (1986) and 91 J. Geophys. Res. 716 (1988), respectively, both of which are incorporated herein by this reference and made a part hereof.

The collisional dissociation chamber 14 consists of a vacuum tight enclosure containing several electrically insulated rings 40 (guard rings) which are maintained at potentials which produce an approximately uniform electric field along the axis of the chamber 14 (the uniformity of this field is not critical). The electric field intensity in this region is typically maintained at 5-20 volt/cm depending on the amount of ion cluster fragmentation desired. This field is sufficiently weak not to dissociate the relatively stable core ions. Even at 5 volt/cm, water clusters are almost completely removed from most ions while ion dissociation is insignificant. Other collisional dissociation chambers can be used, such as, for example, the device described in U.K. Patent No. 1,584,459.

The removal of $H_2O$ clusters is not crucial to the operation of this invention; however, their removal does offer two important benefits: the removal of $H_2O$ clusters from ions of the type: $A^{+/-}{}_n \cdot (H_2O)_m$ (where ions corresponding to n=1, 2, and 3 may all be present at the same time) results in the detection of ion $A^{+/-}$ at only a single mass (essentially all ions evolving in the above manner are single charged) and not as a series of masses which would include integer multiples of mass 18 above the core ion's mass. Thus, the resulting ion spectra will be simple, containing only one ion mass per core ion species, and the number of ions observed at each peak will be larger because they are not divided up among several different mass peaks.

Figure 3:
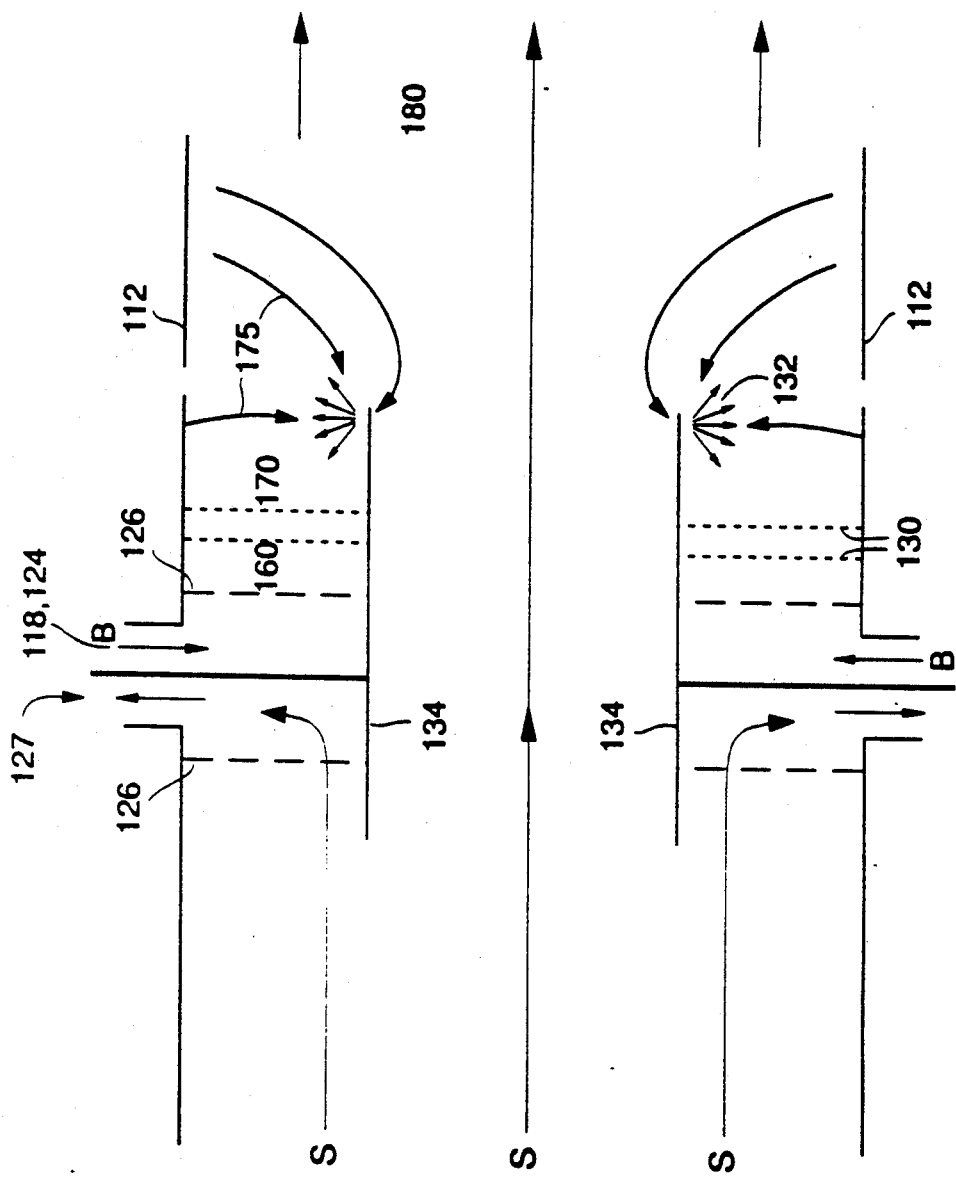
FIG. 3 is a schematic of an alternate embodiment of the present invention used in Example IV.
Figure 4:
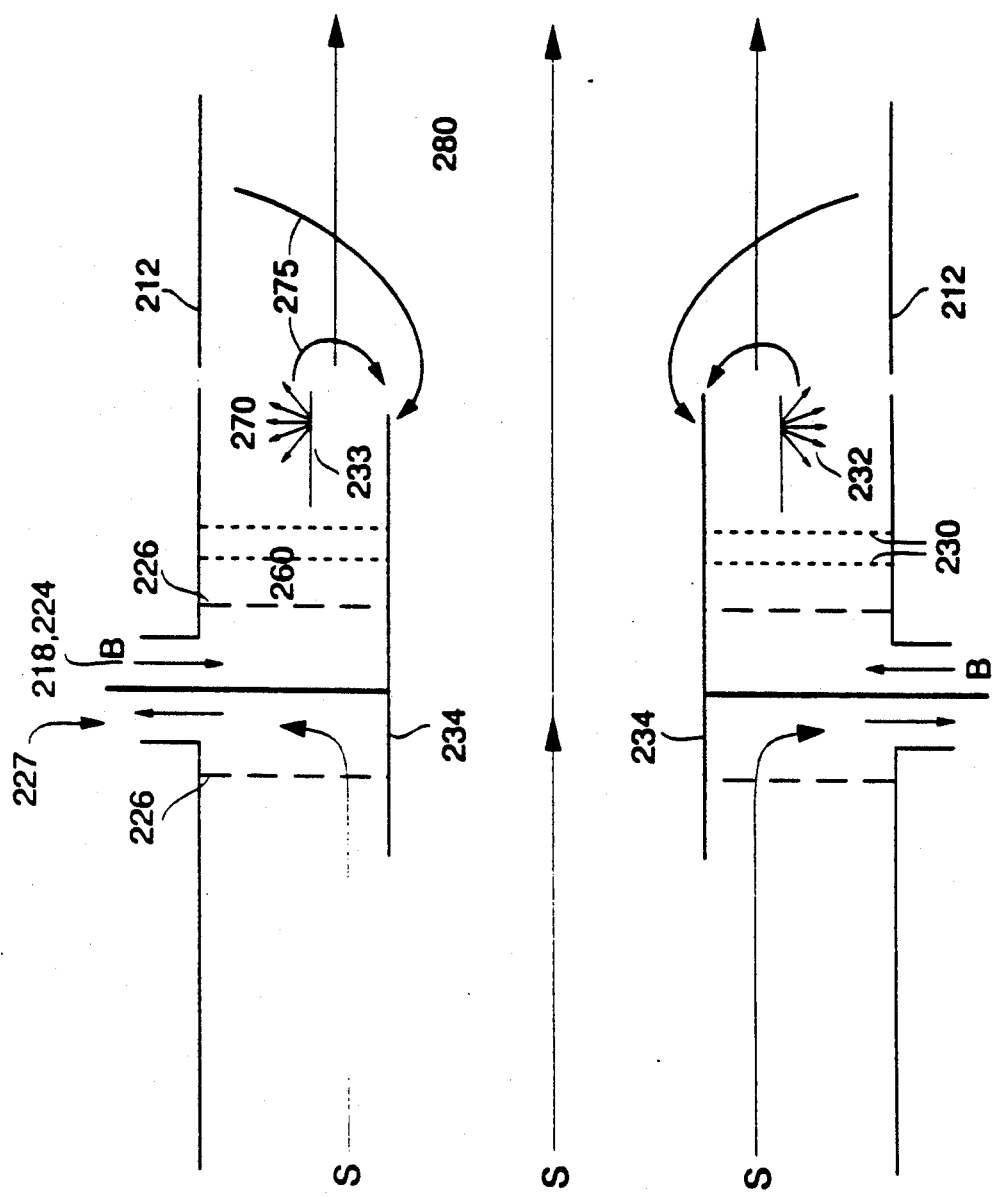
FIG. 4 is a schematic of an alternate embodiment of the present invention shown in FIG. 3, having an alternate ion source.

Turning now to FIGS. 3 and 4, alternate embodiments of the flow tube reactor cell 12 are shown. Corresponding parts in FIGS. 3 and 4 are denoted by adding the numerals 1 and 2, respectively, before the corresponding numeral of FIG. 1. The embodiments shown in FIGS. 3 and 4 generally are used when larger quantities of sample gas such as ambient air are inputted to the flow tube 112, 212. The embodiment shown in FIG. 4 is identical to the embodiment shown in FIG. 3 with the exception of the placement of the radioactive source 232 and the addition of a third cylindrical surface 233 which, as more fully described below, has an effect on the shape of the optional electric field E and the time that ions must spend in the buffer gas before reaching the sample gas. In the embodiments shown in FIGS. 3 and 4, the sample gas, indicated by the three arrows labeled S, is introduced into the flow tube 112, 212 through a relatively wide input port. Part of the sample gas exits the flow tube radially through sample gas exit port 127, 227 while the quantity of the sample gas to be analyzed enters the injection needle 134, 234.

The buffer gas, indicated by the arrows labeled B, radially enters the flow tube through buffer gas input 124, 224 and into the laminar buffer gas flow region 160, 260. In this region 160, 260, the buffer gas first passes through flange 126, 226, which uniformly disperses the buffer gas, and then through turbulence-reducing screens 130, 230, to create a laminar flow of the buffer gas. The buffer gas, now in laminar flow, enters the ion source region where the buffer gas is ionized by the radioactive source 132, 232. The flange 126, 226, turbulence-reducing screen 130, 230 and radioactive source 132, 232 are located concentrically about injection needle 134, 234.

After being ionized in region 170 and 270, the buffer gas enters the specific ion-molecule reaction region 180, 280 where it encounters and reacts with the sample gas. Electric fields E are applied between the flow tube 112, 212 wall and the injection needle 134, 234 to force the buffer gas ion from the ion source region 170, 270 into the much larger sample gas flow for more efficient reaction with the sample gas. The positioning of radioactive source 232 on cylinder 233 makes practical the use of different electric fields E as shown in FIGS. 3 and 4. The buffer gas and sample gas travel along the remainder of the flow tube 112, 212 as described with reference to FIG. 1, and typically are sampled through a curtain gas and a collisional dissociation chamber.

2. Operation

The interface 10 of the present invention is calibrated for each sample species desired to be detected by determining the reaction parameters (reaction rates, reaction times, reaction temperatures, etc.) for the desired species. Each species ion has a different reaction rate constant and electron or proton affinity and may require different reaction parameters, such as, for example, initial reactant ion species, reaction time, injection needle temperature, feed rate of buffer gas and quantity and feed rate of species ion. Once the interface 10 is calibrated for a specific species ion, it can be left at that calibration for detection of that species ion because the calibration depends not on ion detection sensitivity but on the ratio of two ion concentrations.

The flow tube 12 and collisional dissociation chamber 14 generally operate at ambient temperature (22°-32° C.). For lower vapor pressure species, it is useful to heat either the flow tube 12, the injection needle 34, or both.

Conventional known means for heating the flow tube 12 are appropriate. The injection needle 34 may be resistance heated using a two concentric tube configuration because of the small diameter and simple shape of this injection needle 34. Heating the injection needle 34 also has the effect of lowering the possibility and quantity of sample species sticking to the inside wall of the injection needle 34.

The system described thus far is well suited for measuring the highest proton or electron affinity species present in a bulk sample. It has, however, been specifically designed to be coupled to a GC in order to measure species with relatively lower proton and/or electron affinities at concentrations in the low- or sub-pptrv range. In order to apply this system more generally to a wide range of chemical compounds, separation of the individual sample compounds prior to being injected into the flow tube is desired. This can be accomplished by coupling the sample inlet of the described flow tube device to the outlet of a gas chromatographic separator column or the outlet of any other system converting a bulk sample into separate compounds suspended in a gas phase, including post-column derivatization devices. The effluent from this separation device can be switched to bypass the flow tube, if necessary, via valve 74 in FIG. 2 to reduce memory effects from injector 34 and diverted into the tube only when the species of interest is expected to emerge from the column.

EXAMPLES I AND II

Figure 2:
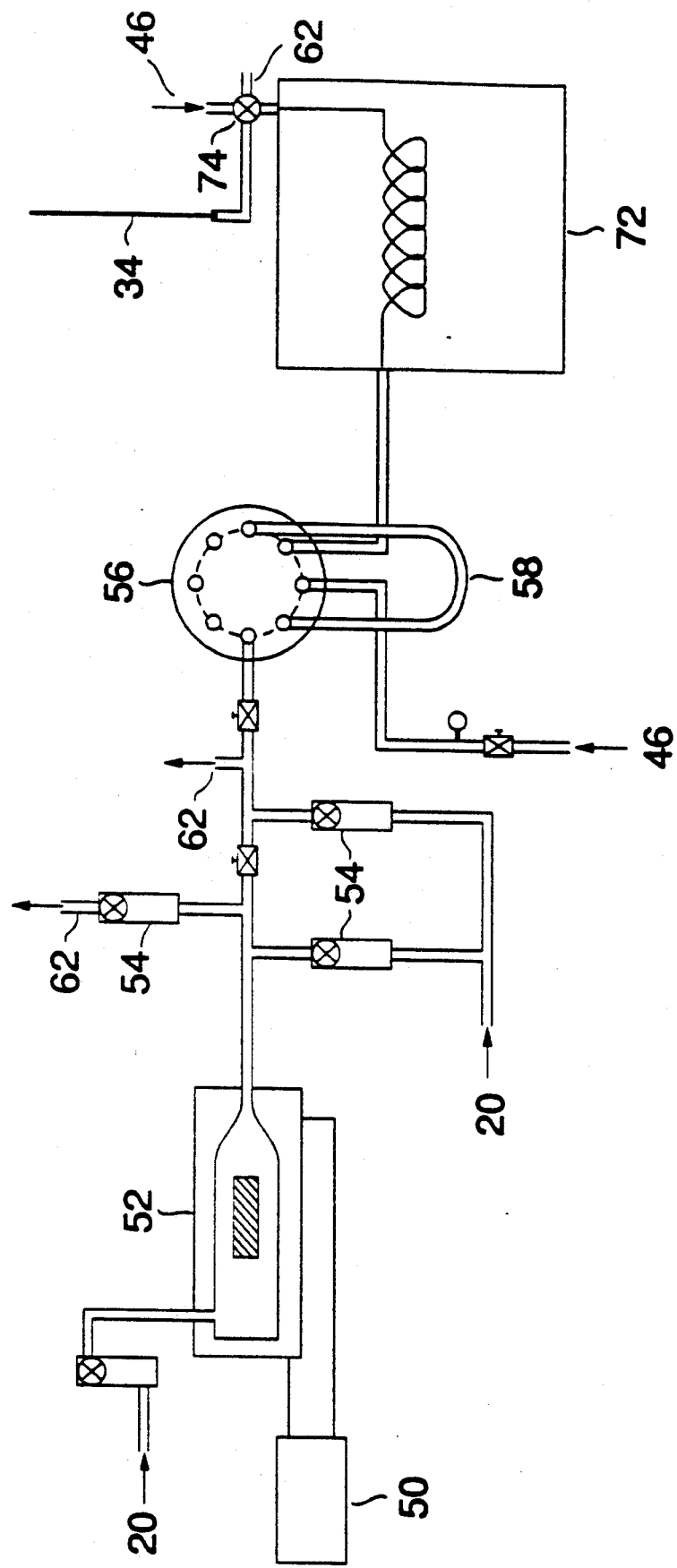
FIG. 2 is a schematic of an alternative embodiment of the sample gas preparation and injection means for the present invention.

Experiments demonstrating the extreme sensitivity and application potential of the described invention in combination with a gas chromatograph (GC) and a mass spectrometer (MS) system were performed using the buffer gas and calibration gas preparation unit as schematically shown in FIG. 2, coupled to the flow tube 12, collisional dissociation chamber 14, and mass spectrometer 16 shown in FIG. 1. Dimethylsulfide (DMS, $CH_3SCH_3$) and beta-caryophyllene (CAR) were used as prototype sample gases in the experiments. Standard dilutions of DMS in the parts-per-trillion range were prepared using a temperature-controlled 50 DMS permeation device 52 and a dynamic gas dilution system including mass flow monitors/controllers 54 and waste exit ports 62 with ultrapure nitrogen as the dilution gas 20. Samples were introduced into a Teflon sample loop 58 connected to the GC gas injection valve 56 and then switched into the GC chromatographic column.

Primary standards of DMS and sulfur dioxide ($SO_2$) were produced using permeation tubes (VICI Metronics). Gas standards of CAR were obtained from the headspace vapor of the liquid (Aldrich) filled into a small open FEP Teflon capsule. Permeation tubes and/or capsule were housed in a permeation oven at constant temperature (about 35° C.) controlled by a YSI model 72 proportional temperature controller in combination with a YSI model 410 temperature probe. All primary standard devices were gravimetrically calibrated by measuring their weight loss with a Mettler H54AR microbalance. Standard dilutions in the parts-per-trillion range were made using the dilution system shown in FIG. 2. The dilution gas 20 was pure nitrogen taken from liquid nitrogen dewars. Flows through the individual components of the dilution system were controlled by mass flow controllers (MKS Instruments). All tubing, fittings, and in-line valves were made of FEP Teflon (Galtek). The calibration standards did not come into contact with any metal components of the system.

DMS and CAR were separated from interfering high proton-affinity species, such as amines, using a Hewlett-Packard Model 5890 gas chromatograph. Best results were obtained with isothermal separation at 90° C. and 140° C., respectively, using a packed column (6 ft. FEP tubing, ⅛" o.d.) filled with Ultrabond 20 M, 100/120 mesh Ultra Scientific). Ultra-high purity helium or nitrogen were used as carrier gases 46 at typical flowrates of 30–60 scc/min. Samples were collected into a 2.3 cc sample loop 58 (⅛" o.d. FEP tubing) without preconcentration and injected into the column through an automatically actuated valve 56. Either a Hamilton 8-port Miniature Inert valve or a 6-port Valco valve were used.

The buffer gas used in the chemical ionization flow tube was purified by passing it through a high pressure (20 psi) liquid nitrogen trap involving about 30 m of coiled ⅛" o.d. stainless steel tubing. The trap was baked out overnight once every 3 to 4 days. For these Examples, there was typically sufficient $H_2O$ present in the buffer gas to produce $H_3O^+$ as the primary reactant ion species present.

Acceptable GC conditions were as follows:
GC mainframe: Model 5890 (Hewlett-Packard);
Injection valve: 8-port, with CTFE core, electrically actuated (Hamilton);
Injection loop: ⅛" FEP tubing, 2.3 cc volume;
Column: ⅛" FEP tubing, 6 ft., bonded Carbowax 20 M Ultrabond (Ultra-Scientific) (a column including Ultrabond 20 M, a bonded Carbowax 20 M phase which due to its quasi-monolayer coating on the solid support (0.2% loading on diatomaceous earth) produces a very low column bleed);
Carrier gas 46: $N_2$ or He, 60 cc/min; and
Oven 72 temperature: 140° C., isothermal.

An important factor in the present apparatus for real-time detection of low proton/electron affinity compounds is the selection of suitable GC column materials. The following minimum requirements should be met by these materials:

1. Inertness towards analyte species such that no analyte loss or memory effects occur at pptrv/sub-pptrv levels;
2. efficient separation of analyte species form high proton or high electron affinity compounds; and
3. low column bleed rendering a high signal-to-noise ratio.

The column end was connected directly to the needle sample orifice 34 of the high pressure chemical ionization flow tube 12. Laminar flow conditions were produced in a flow tube 12 preceding the reaction tube. The columns described above, used for DMS and CAR measurements, showed satisfactory performances. At a typical carrier gas 46 flow rate of 40 scc/min and oven 72 temperature of 90° C., DMS was detected approximately 20–25 seconds after injection. Typical DMS peak widths were 5–10 seconds depending on concentration. Retention times and peak widths for CAR samples were similar for an oven 72 temperature of 140° C. DMS was detected as a sharp peak in the positive spectrum at mass 63 (DMS plus one proton). Integration time for individual measurements was 10 sec. Interferences due to column bleed or loss of DMS in the column and tubing were fairly small.

Figure 5:
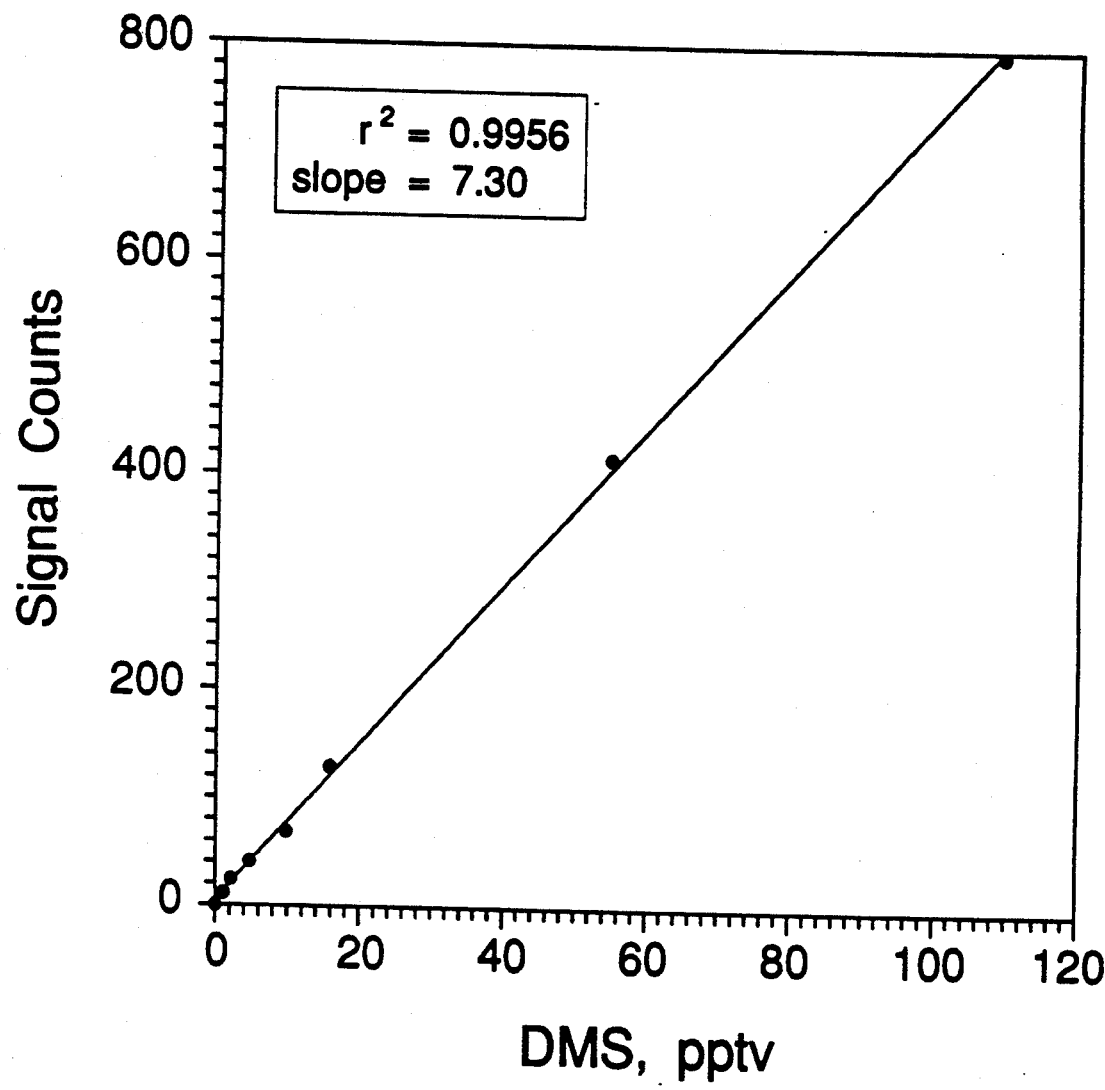
FIG. 5 is a calibration curve for dimethylsulfide (DMS) used as the experimental gaseous sample over a range of 0 to 150 parts per trillion.
Figure 6:
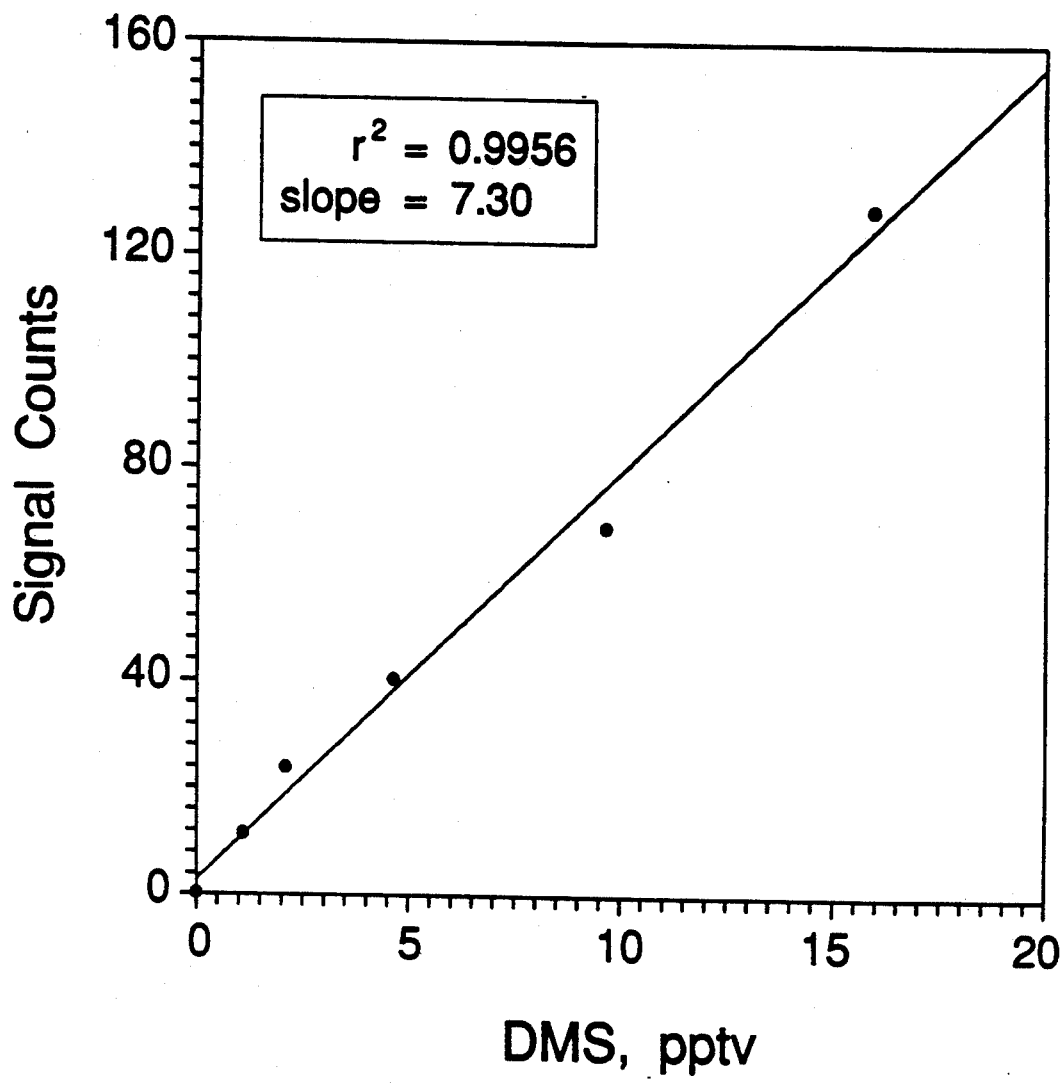
FIG. 6 is an enlarged portion of FIG. 5 over a range of 0 to 20 parts per trillion as an example of the sensitivity of the present invention.

DMS is produced naturally in large amounts by marine phytoplankton and is the most important sulfur gas emitted from the oceans. FIGS. 5 and 6 show a typical calibration curve obtained for DMS using the present apparatus and the GC conditions described earlier. The detection limit (DL) was approximately 0.5 pptv for a signal to noise ratio of 2. A lower DL may be achieved by further optimization of the experimental conditions (e.g., purity of dilution and carrier gases, flow conditions, GC column). DMS also was sampled from ambient laboratory air and clearly separated at the described GC conditions from any other compounds present in the sample. No interferences in the analysis were found. FIG. 5 shows the calibration curve obtained for DMS and exemplifies the linear response of the present invention. FIG. 6 is an enlargement of a portion of FIG. 5 and exemplifies the sensitivity of the present invention. The lowest concentration measured was 1.1 pptrv at 11.4±3.1 signal counts above background (15 sample runs; sample injections: 1 per 80 sec). Standard errors are shown for concentrations <20 pptrv. For these conditions, DMS detection limit is about 0.5 pptrv (S/N=2). The time resolution of the measurements can be increased greatly by consecutively injecting samples into a parallel series of GC columns and switching the eluting DMS peaks into the chemical ionization reactor. This can be achieved simply by using automated distribution valves and zero dead-volume connections.

Figure 7:
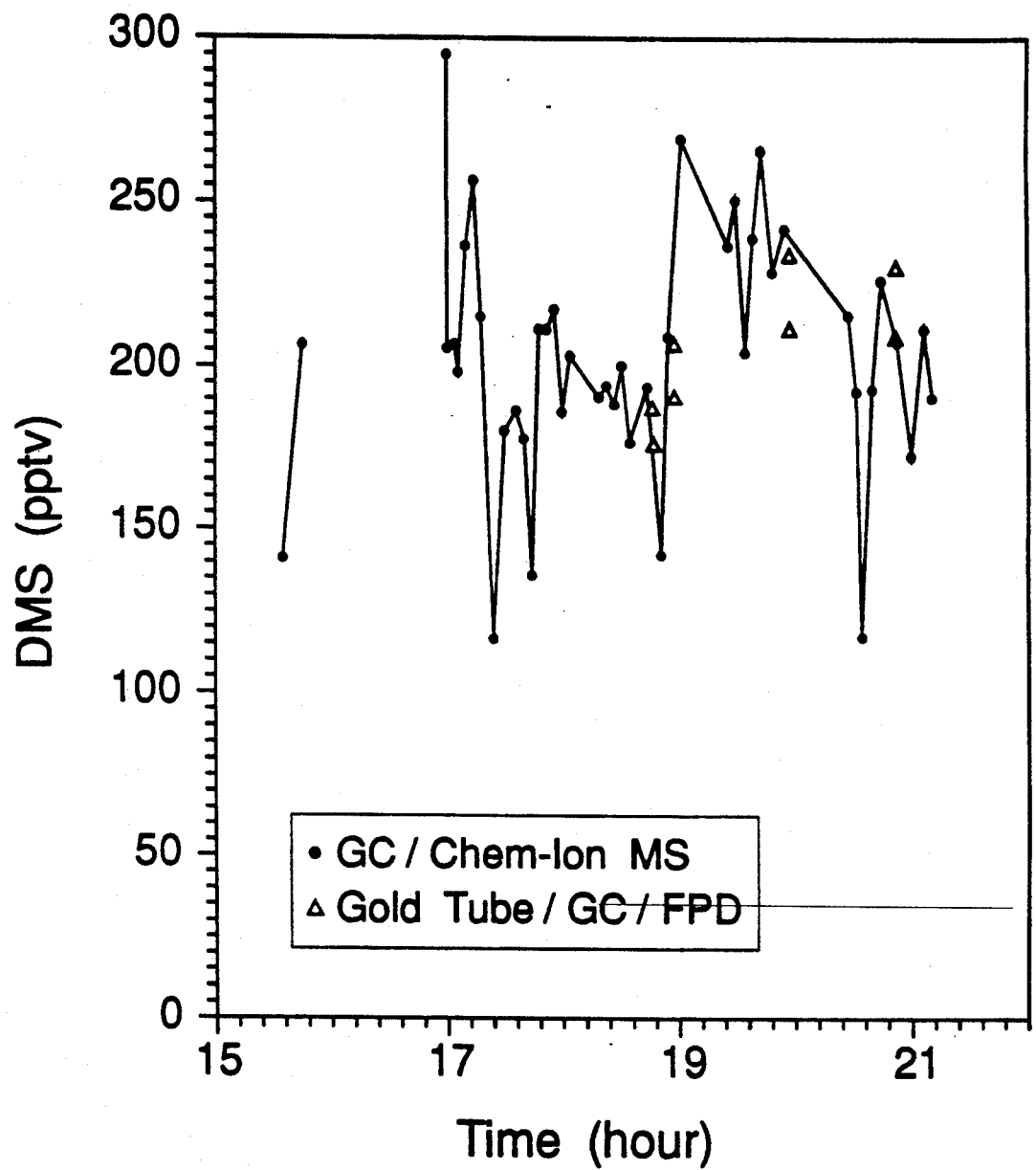
FIG. 7 is an actual field measurement of dimethylsulfide (DMS) using the apparatus of this invention.

FIG. 7 shows the results of field measurements of atmospheric DMS made with the present system at a coastal site on Sapelo Island, Ga., in May, 1990. Also included in FIG. 7 are the results of measurements made at the same location using a preconcentration technique in which DMS is collected by adsorption on a gold surface. The DMS is subsequently desorbed by heating the gold surface, cryofocussed at $-196°$ C., separated on a GC column, and analyzed by a sulfur-specific flame photometric detector (FPD). A Hewlett-Packard FPD was used in this study. GC separation was performed at an oven temperature of $100°$ C. on a 9 ft., $\frac{1}{8}''$ o.d. FEP column packed with Carbopack B/1.5% XE-60/1.0% $H_3PO_4$ (Supelco). Helium was used as the carrier gas at a flowrate of 20 scc/min. The DMS detection limit with this technique is about 1 pptrv for a 20 liter sample. Precision is ±10%.

Figure 8:
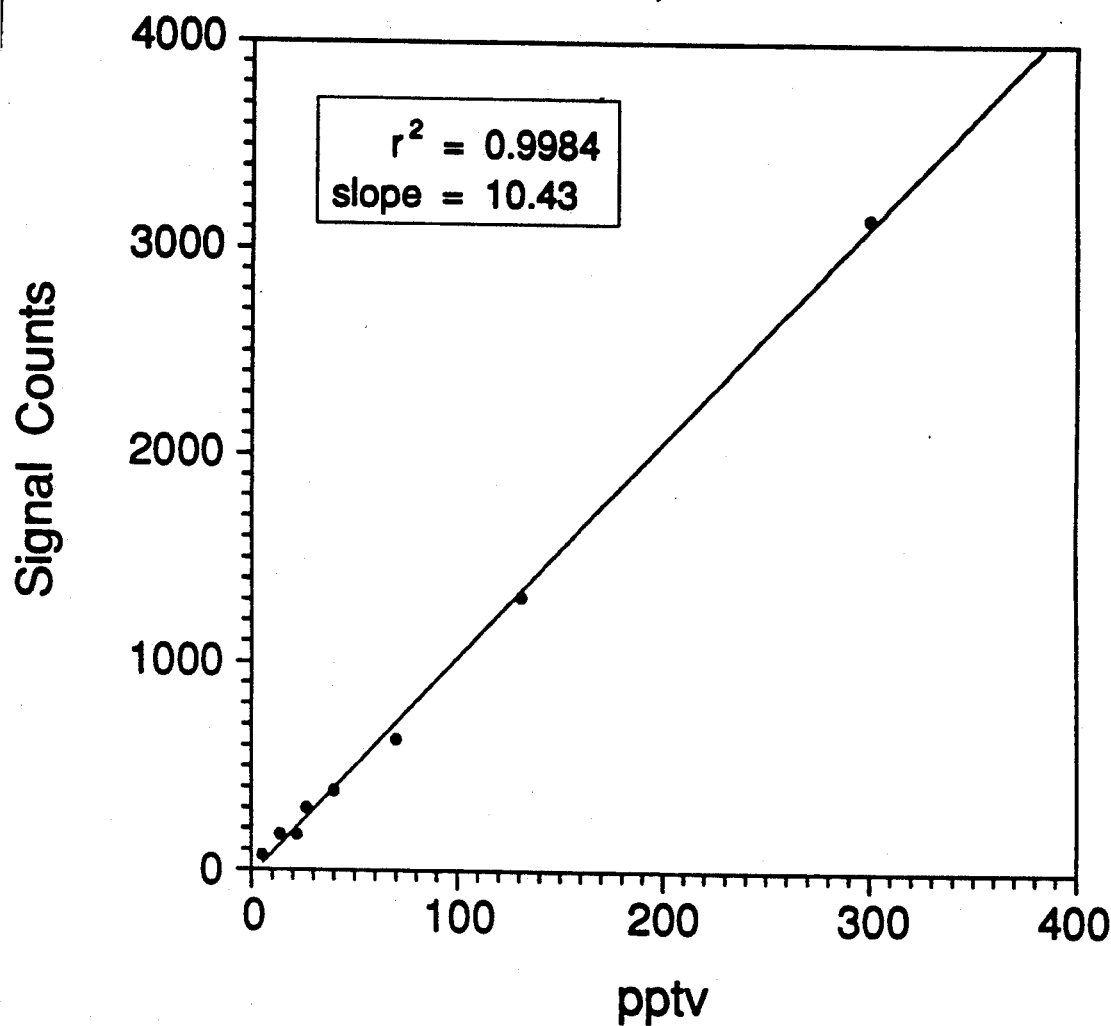
FIG. 8 is a calibration curve for beta-caryophyllene (CAR) used as the experimental gaseous sample over a range of 0 to 400 parts per trillion.

Beta-caryophyllene (CAR) is a high molecular weight hydrocarbon (mol. wt 204; $b.p._{14}$ $130°$ C.) used mainly in perfumery. It occurs naturally in many essential oils, particularly clove oil, and also as a trace substance in certain illegal drugs which makes it an interesting candidate for drug-of-abuse detection in air. CAR detection in oils with conventional GC/FID methods is very time-consuming due to relatively long retention times (20-30 minutes). Its detection in ambient air has not been previously reported. FIG. 8 shows a typical CAR calibration curve. The lowest concentration measured was 4.9 pptrv yielding an average signal count of 73.4±12.5 for 8 repetitive injections (sample injection: 1 per 80 sec). The detection limit is about 0.5 pptrv at these operating conditions. Similar to DMS, the time resolution for CAR measurements can be further improved.

The present invention also bears a high potential for a wide range of applications due to the wide range of applicability and modularity of the major peripheral instruments (GC, mass spectrometer), and the relatively high electron and/or proton affinities of a large number of organic and inorganic compounds which occur in the atmosphere and in other environments. For example, isoprene, one of the most reactive natural hydrocarbons in the atmosphere, has a relatively high proton affinity. Detection of isoprene both in clean standard dilutions and in ambient air (ppbv and pptrv range) have been performed. The invention can be expanded to a number of other species, e.g., sulfur dioxide, dimethylsulfoxide, and various unsaturated hydrocarbons and amine species. Different types of separation columns can be used.

EXAMPLE III

Figure 9:
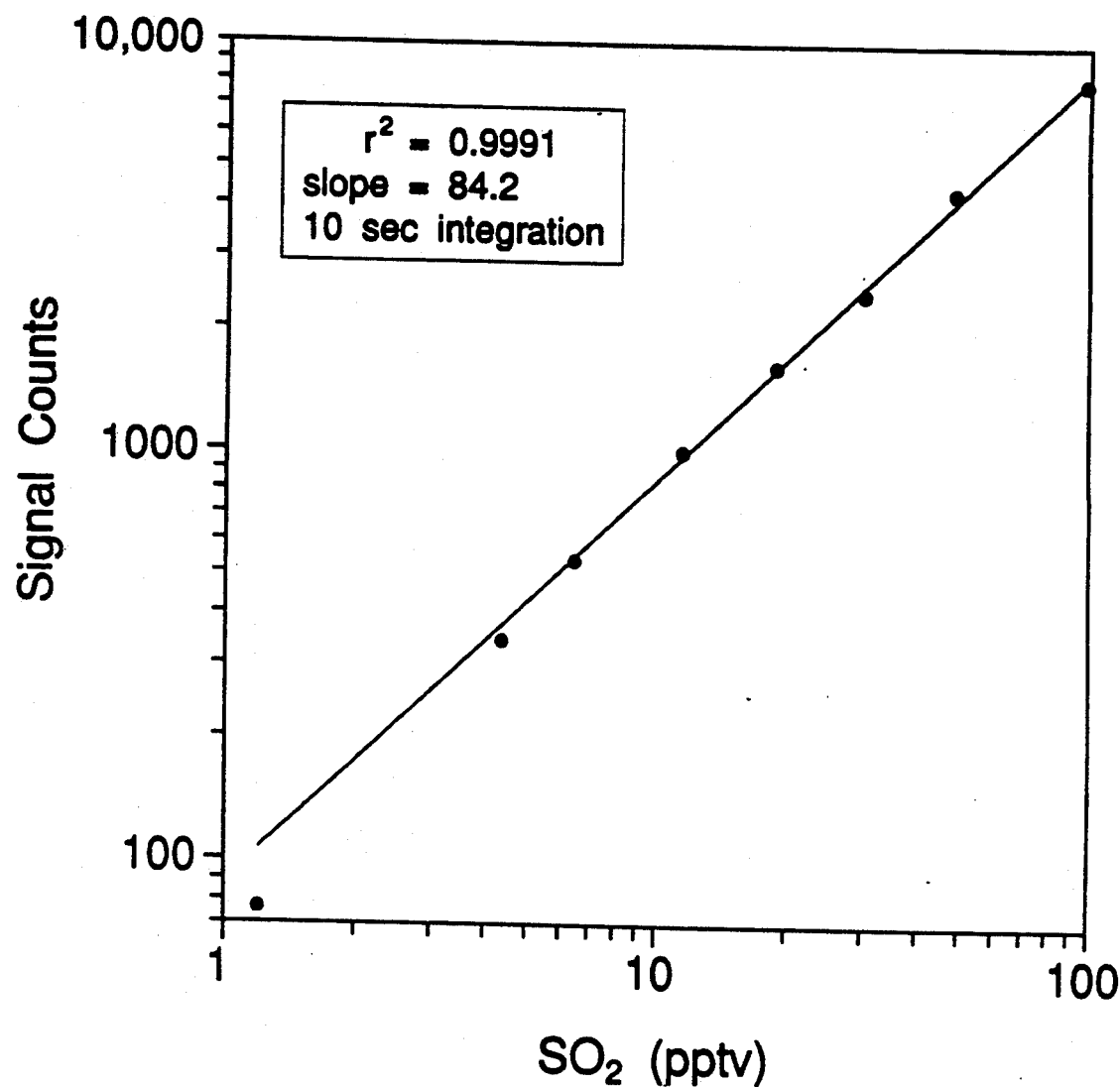
FIG. 9 is a calibration curve for sulfur dioxide used as the experimental gaseous sample over a range of 0.1 to 100 parts per trillion.

A primary standard of $SO_2$ was produced as in the above Examples. A different method was used to measure $SO_2$. No GC separation was necessary. $SO_2$ was derivatized to $SO^-_5$ and detected at 112 amu in the negative spectrum. The resulting calibration curve is shown in FIG. 9. $SO_2$ detection was quasi-continuous (intergration cycle: 10 sec). The lowest concentration measured 1.2 pptrv yielding an average signal of 76.5±7.9 counts in 10 runs. The $SO_2$ detection limit of this method is about 0.2 pptrv at 10 sec integration and was limited by background noise. Interferences by DMS were found to be negligible. Tests showed a signal count equivalent to less than 5 pptrv $SO_2$ when DMS was added to the system at a concentration of 5 ppb. Standard addition measurements were made in laboratory air. The resulting $SO_2$ concentrations (low ppb range) were measured both with the present technique and with a Thermoelectron $SO_2$ fluorescence monitor. A good agreement between the results obtained with both instruments was found.

EXAMPLE IV

Figure 10:
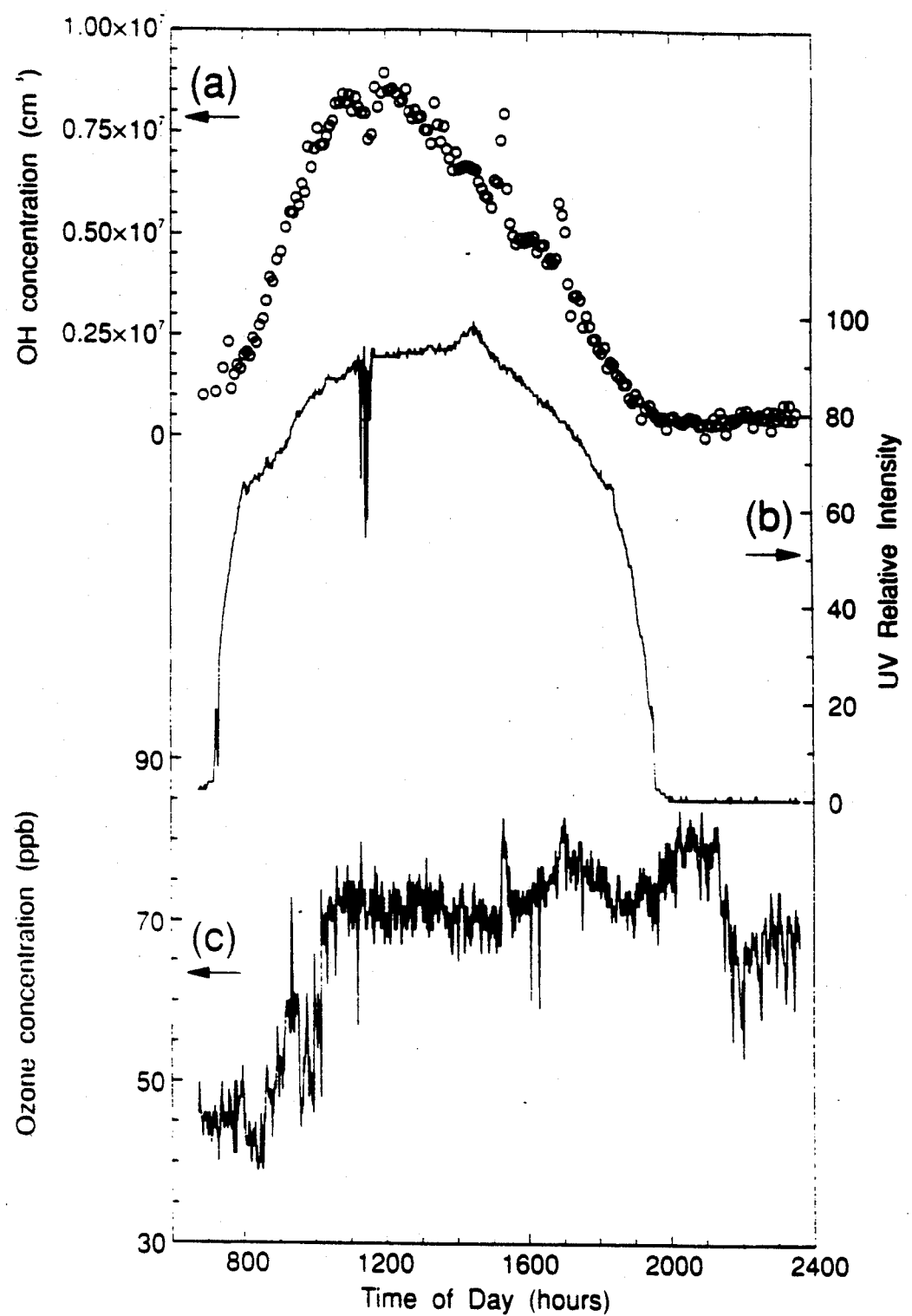
FIG. 10 shows the OH concentration (A), the ultraviolet relative intensity (B), and the ozone concentration (C) for an OH detector run.
Figure 1:
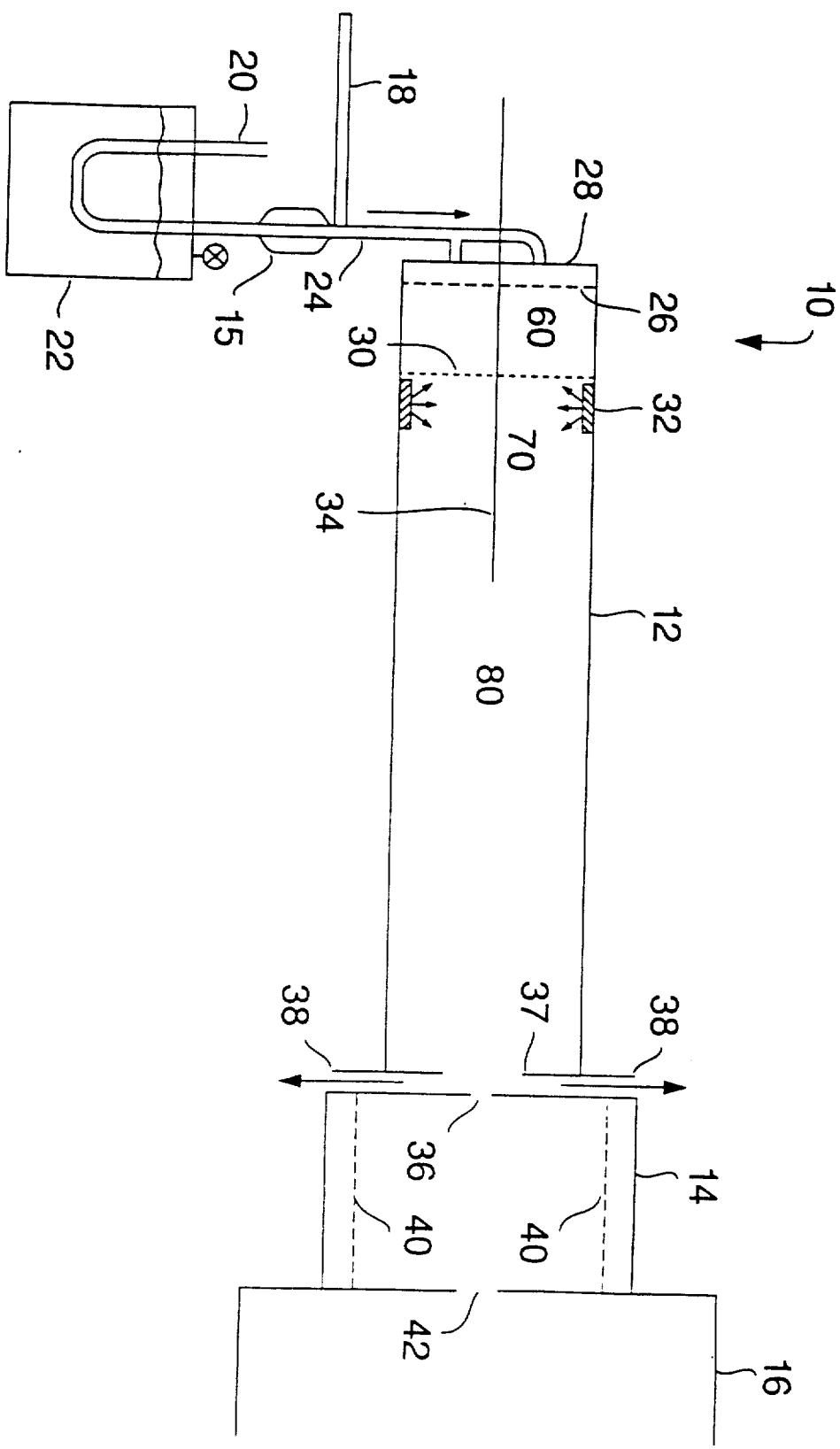

The apparatus described above as shown in FIG. 3 was used in conjunction with an ion analysis apparatus and resulted in the measurement of the OH radical at concentrations of less than 0.01 ppt. FIG. 10 shows the sensitivity of the present invention when used to detect concentrations of specific compounds in a sample of ambient air. FIG. 10 shows that the present invention is able to measure OH at concentrations down to the $1 \times 10^5$ molecules/$cm^3$, which is sufficient sensitivity in time resolution to discern variations in the OH concentration much smaller and faster than any existing method.

Each OH concentration shown in FIG. 10a corresponds to a 300 second measurement time which includes 20 five second OH measurements, 20 five second background measurements, and about 100 seconds for logging and storing OH in meteorological data. FIG. 10b and c show the ultraviolet solar flux and the ozone concentration, revealing a nearly simultaneous drop in OH concentration and ultraviolet flux and simultaneous increases in ozone and OH concentrations.

A brief list showing some various types of compounds which can be studied is given in Table A, which contains a sample, non-exhaustive list of compounds selected from the literature which have proton affinities high enough to be analyzed by the present techniques. Lias, Evacuated Gas Phase Basicities and Proton Affinities of Molecules, Heats of Formation of Protonated Molecules, 13 J. Phys. Chem. Ref. Data 695 (1984). Many other similar compounds can be added to the list as well as a large number of amines and related N-containing groups with proton affinities greater than 214 and less than 171 kcal/mole.

TABLE A

| Affinity | Formula | Name | Importance |
|---|---|---|---|
| 171.4 | CHN | Hydrogen Cyanide | a, w, t |
| 171.7 | CH2O | Formaldehyde | a, w |
| 173.3 | CHNO | Cyanic Acid | a, w, t |
| 175.7 | CClN | Cyanogen Chloride | a, w, t (military poison) |
| 175.8 | C2Cl3N | Trichloroacetonitrile | a, w, t (insecticide) |
| 176 | C2H5I | Ethyliodide | a, w |
| 177.4 | C2H3Cl3O | Trichloroethanol | t |
| 178.3 | CBrN | Cyanogen Bromide | t |
| 178.8 | CH2O2 | Formic Acid | a, w |
| 179.2 | AsH3 | Arsine | a, w, t |
| 179.2 | CH3NO2 | Nitromethane | a, t, e, i (rocket fuel) |
| 179.4 | C4H8 | Butene | a, i |
| 179.5 | C4H5NO2 | Succinimide | d |
| 179.5 | C3H6 | Progene | a, i, f |
| 179.8 | C3H6 (c) | Cyclopropane | a, i, f, e (anesthetic) |
| 180 | C6CrO6 | Chromium Carbonyl | a, i, f, e (gasoline addit.) |
| 180 | C4NiO4 | Nickel Carbonyl | a, f, e, t, c |
| 181.3 | C6H6 | Benzene | a, w, i, f, t, c |
| 181.7 | C6H5Cl | Chlorobenzene | a, i, s (solv. for paints) |
| 181.9 | CH4O | Methanol | a, i, s |
| 182.4 | C2H3ClO2 | Chloroacetic Acid | a, w, i, t (herbicide) |
| 182.4 | C6H5Br | Bromobenzene | a, i (motor oil additive) |
| 183.5 | C2HCl3O2 | Trichloroacetic Acid | w, co (herbicide; caustic) |
| 183.5 | C2H3FO2 | Fluoroacetic Acid | w, t (rodenticide) |
| 184.8 | C2H5NO2 | Nitroethane | t, s |
| 186 | C2H6Hg | Dimethylmercury | a, t, f (in fish, birds) |
| 186 | CH2S | Methylenesulfide | a ??? |
| 186.6 | C2H4O | Acetaldehyde | a, w, i, f, t |
| 187.4 | CH4S | Methanethiol | a, i, t |
| 187.5 | C3H4ClN | Chloropropionitrile | t |
| 187.9 | C2H4O | Ethylene Oxide (Oxirane) | a, i, t, f (fungicide) |
| 188.3 | C2H5OH | Ethanol | a, s |
| 188.4 | C2H3N | Acetonitrile | w, t, s, f |
| 188.9 | C2H4O2 | Methyl Formate | t, f (larvicide) |
| 189.6 | C3H6O | Propionaldehyde | a |
| 189.7 | C3H3N | Acrylonitrile | t, f, e, c (pesticide use) |
| 189.9 | C7H8 | Toluene | a, i, f, t, s (gasol. add.) |
| 190.2 | C2H4O2 | Acetic Acid | a, w, i, f, s |
| 190.8 | C3H8O | 1-Propanol (n) | a, s, f |
| 190.8 | C6H6O | Phenol | w, i, t, co (disinfectant) |
| 190.8 | C2H6S | Ethanethiol | a, i (odorant) |
| 191.1 | C4H10O | 1-Butanol (n) | a, s, f |
| 191.2 | C3H8O | 2-Propanol (iso) | a, f, s (antifreeze agent) |
| 191.5 | C4H8O | Butyraldehyde | a, w, f, t |
| 191.6 | C8H10 | Ethylbenzene | a, f, s |
| 191.6 | C3H8S | Propanethiol | a ??? |
| 191.8 | C3H6O2 | Propionic Acid | a (wood burning prod.) |
| 192.0 | C6H10 | p-Xylene | a, t, s |
| 192.1 | C2H6O | Methyl Ether | a, w (refrigerant) |
| 192.1 | C10H14 | n-Butylbenzene | |
| 192.1 | C9H12 | i-Propylbenzene | |
| 192.2 | C4H4O | Furan | |
| 192.4 | C9H12 | n-Propylbenzene | |
| 192.5 | CH3NO2 | Methylnitrite | a? |
| 192.6 | C5H10O | n-Valeraldehyde | a?, i (flavorant) |
| 192.6 | C4H8O | i-Butyraldehyde | |
| 192.6 | C3H5N | Propionitrile | t |
| 193.0 | C10H14 | tert-Butylbenzene | |
| 193 | C4H6 | Butadiene | a, i |
| 193.1 | C3H6O2 | Ethyl Formate | a?, i, s (flavorant) |
| 193.3 | C8H10 | o-Xylene | a, t, s |
| 193.4 | C6H5NO2 | Nitrobenzene | a?, i, t, s |
| 193.8 | C4H8O2 | 1,4-Dioxane | a, w, i, t, c |
| 193.9 | C3H4O | Acrolein | i, t, f |
| 194.1 | C3H8S | i-Propanethiol | |
| 194.6 | C2H4S | Ethylene Sulfide (Thiirane) | a ??? |
| 194.7 | C10H8 | Naphthalene | a?, i, t |
| 195.9 | C8H10 | m-Xylene | a?, t, s |
| 195.9 | C4H8 | i-Butylene | a, i |
| 195.9 | C2H3NS | Methyl Isothiocyanate | a, t (pesticide) |
| 196 | C2H6S2 | Dimethyldisulfide | a |
| 196.5 | C4H4S | Thiophene | a?, i (in coal, tar) |
| 196.7 | C3H6O | Acetone | a, f, s |
| 197.8 | C3H6O2 | Methyl Acetate | |
| 198.4 | CH3NO | Formamide | i, s |
| 198.7 | C14H10 | Phenanthrene | |
| 198.8 | C4H8O | Tetrahydrofuran | i, s |
| 199.6 | C5H6 | Cyclopentadiene | |
| 200.4 | C5H8 | Isoprene | a |
| 200.6 | C2H6S | Dimethylsulfide | a, w |
| 203.5 | C3H8S | Methyl Ethylsulfide | a |

TABLE A-continued

| Affinity | Formula | Name | Importance |
|---|---|---|---|
| 204.0 | H3N | Ammonia | a |
| 205.0 | C4H10S | Diethylsulfide | a |
| 211.3 | C2H6OS | Dimethylsulfoxide | a, w, s |
| 214.3 | C3H7NO2S | L-Cysteine | w (amino acid) | a = air chemistry, w = water chemistry, t = toxic substance, e = explosive, d = drug, i = industry use, f = flammable, c = carcinogenic, co = corrosive, s = solvent The invention described above in combination with a mass spectrometer 16 system makes it possible to measure and positively identify species having sufficient proton and/or electron affinities (but for lower than those presently observable with existing chemical ionization techniques) at concentrations well below 1 ppt. Thus a wider range of compounds may be viewed, and a higher sensitivity achieved. The ability to accomplish such a high degree of sensitivity has already been demonstrated by the above data and its potential to achieve even greater sensitivity is demonstrated by a very sensitive atmospheric ion sampling apparatus. See 91 J. Geophys. Res. 716 (1988); 94 J. Geophys. Res. 2183 (1989); 96 J. Geophys. Res. 1023–1031 (1991); all of which are incorporated herein by this reference and made a part hereof. While the atmospheric ion sampling portion of the apparatus is quite different from the present invention, the chemical reactions and reaction times are quite similar, and the mass spectrometer used is the same. Thus, a similar sensitivity is anticipated. The interface 10 is capable of increasing the detection sensitivity for a wide range of species ions, including the more stable high affinity species and the less stable low affinity species. Species having negative spectra also can be detected by using the invention. This invention makes practical the detection of currently hard to detect species at a reasonable sensitivity. The invention is capable of increasing the detection sensitivity of a mass spectrometer for sample species ions ionized by both proton gain or loss or electron gain.

3. Alternatives

Flow tube gases can be used that only allow higher proton or electron affinity gases to be observed, or which allow the range to be extended. The buffer gas composition can be modified in order to optimize the detection of species with very low proton or electron affinities. Specific flow tube gas additives can be used which initiate a more complex but specific series of reactions.

Other alternatives to the components of this invention include: use of other ionization sources such as corona sources or X-rays; use of monopolar rather than bipolar ion distribution; use of tandem mass spectrometer instead of a single mass spectrometer; use of multiple side or axial injection ports; and use in combination with a chromatographic system involving known variations of sample injection (e.g., gas injection valves, syringe injection) and injection ports (e.g., on-column injection, flash vaporization of liquids), known types of chromatographic columns (e.g., packed columns, capillary columns) and column materials, and known types of chromatographic methods (e.g., gas chromatography, supercritial fluid chromatography (SFC), liquid chromatography with devices transforming the liquid sample into a gas or fine gaseous suspension).

The above detailed description and examples describe the best mode of the invention contemplated by the inventors at this time and are meant for illustrative purposes and not to limit the invention as defined in the appended claims.

What is claimed:

1. An apparatus for connecting a gaseous medium source located upstream from the apparatus to a mass analysis device located downstream from the apparatus, the apparatus comprising a flow tube ion reactor cell, an isolated ionization source, at least one sample injection means, and a buffer gas inlet means, said flow tube comprises proximal and distal ends and inner and outer surfaces, said proximal end being connected to said buffer gas inlet means and said distal end being connected to said mass analysis device;

said at least one sample injection means being located coaxially with said flow tube and comprising a hollow shaft terminating in a sample outlet port;

said isolated ionization source being located within said flow tube in an ion source region upstream and isolated from said sample outlet port;

said buffer gas injection port being located upstream from said isolated ionization source and from said sample outlet port and configured so as to allow the introduction of a buffer gas coaxially about said sample outlet port;

means for creating a laminar flow of said buffer gas within said flow tube; and an ion-molecule reaction region within said flow tube and located downstream from said sample outlet port.

2. The apparatus as described in claim 1, wherein said buffer gas injection port injects a buffer gas comprising a carrier gas and one or more trace gas parent neutral species into said flow tube.

3. The apparatus as described in claim 1, wherein said ionization source being located on the inside perimeter of said inner surface of said flow tube.

4. The apparatus as claimed in claim 2, wherein said means for creating a laminar flow of said buffer gas within said flow tube is selected so as to create a laminar flow of said buffer gas concentric about said sample outlet port.

5. The apparatus as claimed in claim 4, wherein said means for creating laminar flow comprises at least one back flange and one turbulence reducing screen, said back flange being located substantially adjacent to said proximal end of said flow tube and having substantially the same shape as the cross-section of said flow tube;

said back flange being a generally solid article having a plurality of holes therethrough to allow said buffer gas to pass from said buffer gas injection port through said back flange into said flow tube so as to substantially uniformly fill said flow tube;

said turbulence reducing screen being located downstream from said back flange and having substantially the same shape as the cross-section of said flow tube;

said turbulence reducing screen having a mesh so as to allow said buffer gas to flow therethrough and to reduce turbulence as said buffer gas flows therethrough resulting in a generally laminar flow; and both said back flange and said turbulence reducing screen being located upstream from said isolated ionization source and said sample injection ports.

6. The apparatus as claimed in claim 5, wherein said sample injection port injects a sample gas axially within said flow tube downstream from said isolated ionization source, said turbulence reducing screen, said back flange, and said buffer gas injection port.

7. The apparatus as claimed in claim 6, wherein said sample gas is injected at a gas flow velocity substantially equal to the flow velocity of said buffer gas and axially within the flow of said buffer gas.

8. The apparatus as claimed in claim 6, further comprising a means for purifying said buffer gas prior to introducing said buffer gas to said flow tube.

9. The apparatus as claimed in claim 8, wherein said means for purifying said buffer gas comprises a cryogenic trap.

10. The apparatus as claimed in claim 4, wherein said isolated ionization source is a radioactive source.

11. The apparatus as claimed in claim 4, further comprising an exit aperture located at said distal end of said flow tube leading into said mass analysis device.

12. The apparatus as claimed in claim 11, further comprising a buffer gas exit port located at said distal end of said flow tube.

13. The apparatus as claimed in claim 11, wherein said exit aperture is located along the axis of said flow tube.

14. The apparatus as claimed in claim 12, wherein said buffer gas exit port is located along the distal perimeter of said flow tube.

15. A method for introducing a gaseous sample to a mass analysis device comprising the steps of:
 (a) providing a sample gas;
 (b) providing a buffer gas comprising a carrier gas and one or more trace gas neutral species;
 (c) providing a buffer gas ionization mechanism;
 (d) providing a flow tube ion reactor cell;
 (e) introducing said buffer gas into said flow tube ion reactor cell as a buffer gas flow;
 (f) providing a means for uniformly diffusing said buffer gas within said flow tube ion reactor cell and for causing said buffer gas to have a laminar flow in an axial direction along said flow tube ion reactor cell;
 (g) ionizing said buffer gas by said buffer gas ionization mechanism within an ion source region, producing an ionized buffer gas flow;
 (h) introducing said sample gas within said flow tube ion reactor cell generally along the central axis of said ionized buffer gas flow;
 (i) reacting said sample gas with said ionized buffer gas by a sample ionization mechanism within an ion/molecule reaction region resulting in the ionization of said sample gas by ion/molecule reactions; and
 (j) introducing said ionized sample gas and ionized buffer gas into said mass analysis device.

16. The method as claimed in claim 15, further comprising the step of drying said carrier gas prior to introducing said buffer gas to said flow tube ion reactor cell.

17. The method as claimed in claim 16, further comprising the step of cleaning said carrier gas prior to introducing said buffer gas to said flow tube ion reactor cell.

18. The method as claimed in claim 15, wherein said ionization of said trace gas is achieved by a radioactive source.

19. The method as claimed in claim 15, further comprising the step of removing said buffer gas prior to introducing said ionized sample gas to said mass analysis device.

20. The method as claimed in claim 18, further comprising the step of removing any water clusters weakly bound to said ionized sample gas prior to introducing said ionized sample gas to said mass analysis device.

21. The method as claimed in claim 15, wherein said sample gas is introduced at substantially the same flow velocity as said buffer gas.

22. A measurement system used to calculate sample species concentration from measured instrumental parameters and a single physical constant, comprising:
 (a) a buffer gas including a carrier gas and at least one trace gas parent neutral species;
 (b) a flow tube reaction cell comprising a laminar buffer gas flow region, an ion source region, and a separate ion/molecule reaction region;
 (c) a means for ionizing said buffer gas to create reactant ions; and
 (d) a means for ionizing said sample gas by reaction with said reactant ions to create product ions, wherein the ratio of said product ions to said reactant ions remaining after reaction with said sample gas, together with the reaction rate coefficient and reaction time, is used to calculate the concentration of said sample species in said sample gas.

23. The system as claimed in claim 22, wherein said buffer gas is introduced into said laminar buffer gas flow region of said flow tube reaction cell, said means for ionizing said buffer gas is located in said ion source region of said flow tube reaction cell, and said sample gas is introduced into said flow tube reaction cell prior to said separate ion/molecule reaction region and within said laminar buffer gas flow region.

24. The system as claimed in claim 23, further comprising a cryogenic trap for purifying said carrier gas.

25. The system as claimed in claim 23, further comprising an exit duct and an exit aperture located in said reaction region of said flow tube reaction cell.

26. A measurement method which used the concentration ratio of at least two ions to calculate the concentration of one of at least one parent neutral species contained in a sample gas comprising the steps of:
 (a) providing a buffer gas including a carrier gas and at least one trace gas neutral reactant species;
 (b) creating a laminar flow of said buffer gas;
 (c) ionizing said buffer gas within an ion source region so as to create buffer gas species reactant ions;
 (d) reacting said sample gas with said buffer gas reactant species ions within an ion/molecule reaction region separate from said ion source region to create sample gas ion species;
 (e) introducing said sample gas ion species and said buffer gas species reactant ions to a detection means; and
 (f) using the concentration ratio of said sample gas ion species to said buffer gas species reactant ion remaining after reaction with said sample gas and the reaction rate and reaction time to determine the concentration of said at least one parent neutral species.

27. The method as claimed in claim 26, further comprising the step of cleaning said buffer gas prior to step (b).

28. The method as claimed in claim 26, further comprising the step of removing metastable, radical, or extraneous species from said sample ion species prior to step (d).

* * * * *

UNITED STATES PATENT AND TRADEMARK OFFICE
CERTIFICATE OF CORRECTION

PATENT NO. : 5,175,431
DATED : December 29, 1992
INVENTOR(S) : Fred L. Eisele; Harald Berresheim It is certified that error appears in the above-indentified patent and that said Letters Patent is hereby corrected as shown below:

In the drawings, Sheet 1, Fig. 1, the reference numeral 70 should be applied to the region which is separated from region 60 by turbulence-reducing screens 30. Column 3, line 40, after "sources" insert --can--; and line 51, change "of" to --or--. Column 8, line 13, change "0.1" to --1.0--. Column 13, line 31, after "gas" insert --radially--. Column 18, line 43, change "in" to --and--.

Signed and Sealed this

Seventh Day of December, 1993

Attest:

BRUCE LEHMAN

Attesting Officer       Commissioner of Patents and Trademarks